United States Patent [19]

Cantwell et al.

[11] Patent Number: 5,468,632
[45] Date of Patent: Nov. 21, 1995

[54] RECOMBINANT DNA COMPOUNDS AND EXPRESSION VECTORS ENCODING PARA-NITROBENZYL ESTERASE ACTIVITY FROM BACILLUS

[75] Inventors: Cathleen A. Cantwell; Roland L. Hodges, both of Indianapolis; Derek McGilvray, Martinsville; Stephen W. Queener; James R. Swartling, both of Indianapolis; Joseph M. Zock, Greenwood, all of Ind.

[73] Assignee: Eli Lilly and Company, Indianapolis, Ind.

[21] Appl. No.: 124,674

[22] Filed: Sep. 22, 1993

Related U.S. Application Data

[63] Continuation-in-part of Ser. No. 975,206, Nov. 12, 1992, abandoned, which is a continuation-in-part of Ser. No. 811,096, Dec. 20, 1991, abandoned.

[51] Int. Cl.$^6$ .............................. C12N 15/55; C12N 9/18; C12N 1/21; C12N 15/63
[52] U.S. Cl. .................... 435/197; 435/69.1; 435/71.2; 435/43; 435/252.3; 435/252.33; 435/320.1; 435/172.3; 536/23.2; 935/14; 935/29; 935/43; 935/56; 935/73
[58] Field of Search .................. 536/23.2; 435/69.1, 435/71.2, 43, 197, 252.3, 252.33, 320.1, 172.3; 935/14, 29, 43, 56, 73

[56] References Cited

U.S. PATENT DOCUMENTS

| | | | |
|---|---|---|---|
| 3,972,774 | 8/1976 | Brannon | 195/29 |
| 4,757,012 | 7/1988 | Estell et al. | 435/172.3 |
| 4,839,293 | 6/1989 | Cantor et al. | 435/240.2 |

OTHER PUBLICATIONS

Berger, S. L. et al. (eds.) "Guide to Molecular Cloning Techniques" Meth. in Enzymology vol. 152 pp. 393–399, 415–423, 432–447 661–704 (1987).

Belyansky, A. et al. "PCR based cDNA library construction: . . . " Nuc. Acids Res. vol. 17(8):2919–2932 (Apr. 1989).

Deutscher, M. P. (ed.) "Guide to Protein Purification". Meths. in Enzymol. vol. 182 pp. 9–15, 285–421, 459–477, 602–613, 738–751 (1990).

J. Sambrook et al. (eds.) "Molecular Cloning: A Laboratory Manual" Cold Spring Harbor Laboratory Press (Oct. 1989) Chapter 17, pp. 17.1–17.44.

Brannon, D. R., et al., J. Antiobiotics, vol. 29(2), pp. 121–124 (1976).

Primary Examiner—Robert A. Wax
Assistant Examiner—Rebecca Prouty
Attorney, Agent, or Firm—Thomas G. Plant; Gerald V. Dahling

[57] ABSTRACT

The present invention provides isolated DNA compounds and recombinant DNA cloning and expression vectors that encode PNB esterase from *Bacillus subtilis*. The invention also provides host cells transformed with these vectors and a method for production of the PNB esterase by recombinant DNA techniques.

26 Claims, 3 Drawing Sheets

RECOMBINANT DNA COMPOUNDS AND EXPRESSION VECTORS ENCODING PARA-NITROBENZYL ESTERASE ACTIVITY FROM BACILLUS

This application is a continuation-in-part of application Ser. No. 07/975,206, filed on Nov. 12, 1992, now abandoned, which is a continuation-in-part of application Ser. No. 07/811,096, filed on Dec. 20, 1991, now abandoned.

BACKGROUND OF THE INVENTION

This invention relates to the field of recombinant DNA technology. In particular, it relates to DNA compounds encoding the enzyme para-nitrobenzyl-esterase (PNB-esterase) from the genus Bacillus. Esters are commonly employed intermediates in the synthesis of cephalosporin and 1-carbacephalosporin antibiotics in free acid form. The preparation of cephalosporins is taught broadly by Chauvette, U.S. Pat. No. 4,064,343. The preparation of 1-carbacephalosporins is taught broadly by Christensen et al., in U.S. Pat. No. 4,226,866, Munroe, in U.S. Pat. No. 4,791,106, and Hirata et al., U.S. Pat. No. 4,708,956.

The PNB-ester function is generally employed to block or protect the acidic carboxylic acid function in the molecule while reactions at other sites of the molecule are carried out. For example, Garbrecht, U.S. Pat. No. 3,632,850, describes the use of the p-nitrobenzyl ester group in the synthesis of cephalexin. In the first step of the synthesis, this ester is cleaved via hydrogenolysis under acidic conditions. In U.S. Pat. No. 3,781,282, Garbrecht describes the de-esterification of p-nitrobenzyl esters of cephalosporins with zinc and acid in an amide-type solvent, such as dimethylformamide. Jackson, U.S. Pat. No. 3,799,924, describes the removal of the p-nitrobenzyl ester group of cephalosporin esters by treatment with sodium or potassium dithionite at a pH above about 7. Hatfield, U.S. Pat. No. 4,091,214, describes a process for de-esterifying esters of cephalosporin compounds which comprises a reductive cleavage employing an inert solvent with zinc and an α-hydroxycarboxylic acid. Hirata et al., U.S. Pat. No. 4,708,956, describes methods for removal of para-nitrobezyl protecting groups from 1-carbacephalosporin compounds. Attendant with these procedures is the high cost of recycling solvents and the potential problem of pollution caused by organic solvents.

An enzymatic method for removal of PNB blocking groups used in the synthesis of cephalosporin and 1-carbacephalosporin antibiotics would have distinct advantages. Such a reaction, proceeding under mild conditions, could be completed in an aqueous reaction mixture without the use of organic solvents and metallic catalysts. Brannon, U.S. Pat. No. 3,972,774, described a process for the removal of the PNB-ester from cephalosporin esters which comprises reacting the ester with a crude preparation derived from a microorganism of the genus Bacillus. However, the enzyme responsible for this cleavage was not isolated.

A purified PNB-esterase from a microorganism of the genus Bacillus is disclosed in United States Patent Application Attorney Docket No. X-8554, entitled "Purified para-Nitrobenzyl Ester From Bacillus", which was filed on the same day as the present application, and which is incorporated herein by reference. This PNB esterase is a monomer having a molecular weight of about 54,000 daltons. Studies indicate that this PNB-esterase catalyzes the de-esterification of PNB-esters of cephalosporin and 1-carbacephalosporin compounds to the free acid form. A process for purifying the enzyme from the Bacillus species is also provided by United States Pat. Appln. Attorney Docket No. X-8554. This process comprises a combination of ammonium sulfate fractionation, pH treatment, anion-exchange chromatography, gel filtration, adsorption-desorption chromatography, and affinity chromatography.

SUMMARY OF THE INVENTION

It has not been possible to use the isolated PNB esterase enzyme isolated from Bacillus in an industrial scale process, because of the low level of the enzyme produced by *Bacillus subtilis*. The present invention remedies this limitation by providing recombinant DNA compounds and vectors encoding a para-nitrobenzyl esterase from *Bacillus subtilis*. The newly isolated DNA sequence provided herein can be used to produce PNB esterase activity in large amounts in recombinant host cells. This PNB esterase is useful for the removal of PNB ester blocking groups used in the manufacture of cephalosporin and 1-carbacephalosporin antibiotics.

The invention described herein teaches how to isolate a gene from *Bacillus subtilis* encoding a PNB esterase that efficiently catalyzes hydrolysis of loracarbef nucleus PNB ester (trans-7-amino-3-chloro-8-oxo-1-azabicyclo<4.2.0>oct- 2-ene-2-carboxylic acid, (4-nitrophenyl)methyl ester monohydrochloride) to loracarbef nucleus free acid (trans- 7-amino-3-chloro-8-oxo-1-azabicyclo<4.2.0>oct-2-ene-2-carboxylic acid monohydrochloride) and PNB alcohol. The enzyme also catalyzes hydrolysis of a 7-amino-3-chlorocephem- 4-carboxylic acid, (4-nitrophenyl) methyl ester, used in the manufacture of cefaclor, so that the corresponding free acid and PNB alcohol are formed. This enzyme also catalyzes hydrolysis of cephalexin PNB ester used in the manufacture of cephalexin, to the corresponding free acid and PNB alcohol. The loracarbef nucleus free acid is a substrate for penicillin G amidase in a reaction in which phenylglycine methyl ester reacts with this compound to form loracarbef and methanol. Likewise, penicillin G amidase catalyzes conversion of phenylglycine methyl ester and cefaclor nucleus free acid or cephalexin nucleus free acid to methanol and cefaclor or cephalexin.

Host-vector systems disclosed by this invention produce PNB esterase very efficiently so that the PNB esterase can represent from about 10 to 20% of the soluble protein in the recombinant *Escherichia coli* strains. This level of gene expression for active PNB esterase, measured by removal of the blocking group from the chemical intermediate loracarbef-PNB, is approximately 190-fold greater than that in *Bacillus subtilis* NRRL B8079. Moreover, because of the high level produced, the enzyme can be purified using a procedure that is considerably simpler and less expensive than that required for purification from *Bacillus subtilis* strain NRRL B8079.

The DNA compounds of the present invention encode the PNB esterase activity in a single open reading frame (orf). Transcription of this open reading frame, followed by the translation of the resulting mRNA, yields a single polypeptide chain that possesses PNB esterase activity. The DNA compound that encodes the PNB esterase activity was isolated from *Bacillus subtilis* genomic DNA and was used in the construction of the recombinant DNA expression vectors. The PNB esterase-encoding DNA compounds of this invention can be used to construct a wide variety of expression vectors which will be useful for the production of PNB esterase.

The invention includes DNA compounds that comprise a DNA sequence encoding PNB esterase activity of *Bacillus subtilis*. Also provided are recombinant DNA vectors, and recombinant host cells which contain these recombinant DNA vectors, such as *Escherichia coli*. Specific vectors that are provided by this invention include the plasmids pNB106R and pNB106RM. These vectors are useful in a method for constructing a recombinant host cell capable of expressing PNB esterase activity, said method comprising:

transforming said host cell with a recombinant DNA expression vector that comprises:
(a) a promoter and translational activating sequence that functions in said host cell; and
(b) a DNA sequence encoding PNB esterase activity of *Bacillus subtilis* positioned for the expression from said promoter and translational activating sequence.

Another useful method of this invention includes a method of using a host cell constructed by the above method, for expressing PNB esterase activity, said method comprising: culturing said host cell under conditions suitable for gene expression.

For the purposes of this invention as disclosed and claimed herein, the following items are defined.

Amp—the ampicillin resistance conferring gene; also used to denote the ampicillin resistant phenotype.

cI857—a gene encoding a temperature sensitive repressor of the bacteriophage lambda pL promoter.

Cloning—the process of incorporating a segment of DNA into a recombinant DNA cloning vector.

Coding sequence—the sequence of DNA in a gene that encodes the amino acid residue sequence of the protein expressed from the gene.

Gene—a segment of DNA that comprises a promoter, translational activating sequence, coding sequence, and 3' regulatory sequences, positioned to drive expression of the gene product.

Genomic library—a set of recombinant DNA cloning vectors into which segments of DNA, which substantially represent the entire genome of a particular organism, have been cloned.

Hybridization—the process of annealing two single-stranded DNA and/or RNA molecules to form a double-stranded molecule that may or may not be completely base paired.

loracarbef—(7B)-7-<D-(aminophenylacetyl)amino>-3 -chloro-8-oxo-1-azabicyclo<4.2.0>oct-2-ene-2-carboxylic acid.

loracarbef nucleus—trans-7-amino-3-chloro-8-oxo-1-azabicyclo< 4.2.0>oct-2-ene-2-carboxylic acid monohydrochloride.

loracarbef PNB ester—7-[(aminophenylacetyl)amino]-3 -chloro-8-oxo-1-azabicyclo<4.2.0>oct-2-ene-2-carboxylic acid(4-nitrophenyl)methyl ester.

mRNA—messenger ribonucleic acid.

ORI—a plasmid or vector origin of replication, the DNA sequence that serves as an attachment or start site for DNA polymerase.

pL—leftward promoter from bacteriophage lambda.

pnbA—the gene encoding PNB esterase activity.

Promoter—a DNA sequence that directs or initiates the transcription of DNA.

Recombinant DNA Cloning Vector—any autonomously replicating or integrating agent, including but not limited to plasmids, comprising a DNA molecule to which one or more additional DNA molecules can be added.

Recombinant DNA Expression Vector—any autonomously replicating or integrating agent, including but not limited to plasmids, comprising a promoter and other regulatory sequences positioned to drive expression of a DNA segment that encodes a polypeptide or RNA.

Recombinant DNA sequence—any DNA sequence, excluding the host chromosome from which the DNA is derived, which comprises a DNA sequence which has been isolated, synthesized, or partially synthesized.

Restriction Fragment—any linear DNA molecule generated by the action of one or more enzymes.

rop—DNA region encoding a plasmid copy control element derived from *Escherichia coli*.

TetR—the tetracycline resistance conferring gene; also used to denote the tetracycline resistant phenotype.

Transcription activating sequence—a promoter.

Transcription terminator—a DNA sequence that signals the termination of transcription of DNA by RNA polymerase.

Transformant—a recipient host cell that has undergone transformation.

Transformation—the introduction of DNA into a recipient host cell that changes the genotype of the recipient cell.

Translational activating sequence—a regulatory DNA sequence that, when transcribed into mRNA, promotes translation of mRNA into protein.

DESCRIPTION OF THE FIGURES

The restriction enzyme and function maps presented in the drawings are approximate representations of the recombinant DNA vectors discussed herein. The restriction site information is not exhaustive, there may be more restriction enzyme sites of a given type than are actually shown on the map.

DETAILED DESCRIPTION

Figure 1:
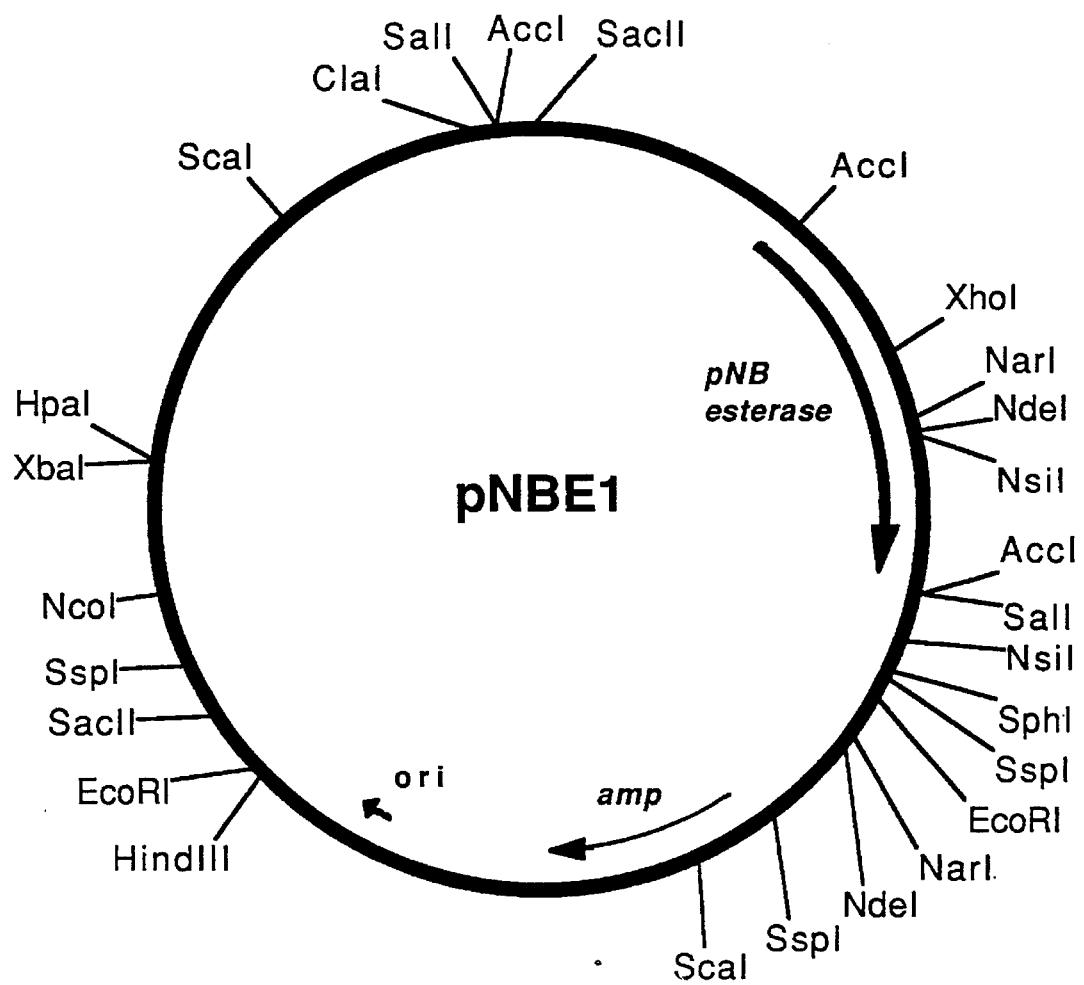
FIG. 1 is a restriction enzyme site and function map of plasmid pNBE1.

The present invention comprises isolated DNA compounds and recombinant DNA cloning and expression vectors that encode the PNB esterase of *Bacillus subtilis*. The sequence of the *B. subtilis* PNB esterase-encoding DNA is depicted below and has been designated as SEQ ID NO: 1. Only the coding strand of the double stranded DNA molecule is shown, and the DNA is depicted from right to left in the 5' to 3' orientation.

| ATG | ACT | CAT | CAA | ATA | GTA | ACG | ACT | CAA | TAC | GGC | AAA | GTA | AAA | 42 |
|-----|-----|-----|-----|-----|-----|-----|-----|-----|-----|-----|-----|-----|-----|-----|
| GGC | ACA | ACG | GAA | AAC | GGC | GTA | CAT | AAG | TGG | AAA | GGC | ATC | CCC | 84 |
| TAT | GCC | AAG | CCG | CCT | GTC | GGA | CAA | TGG | CGT | TTT | AAA | GCA | CCT | 126 |
| GAG | CCG | CCT | GAA | GTG | TGG | GAA | GAT | GTC | CTT | GAT | GCC | ACA | GCG | 168 |
| TAC | GGT | CCT | ATT | TGC | CCG | CAG | CCG | TCT | GAT | TTG | CTC | TCA | CTG | 210 |

| | | | | | | | | | | | | | | |
|---|---|---|---|---|---|---|---|---|---|---|---|---|---|---|
| TCG | TAT | ACA | GAG | CTG | CCC | CGC | CAG | TCC | GAG | GAT | TGC | TTG | TAT | 252 |
| GTC | AAT | GTA | TTT | GCG | CCT | GAC | ACT | CCA | AGT | CAA | AAT | CTT | CCT | 294 |
| GTC | ATG | GTG | TGG | ATT | CAC | GGA | GGC | GCT | TTT | TAT | CTT | GGA | GCG | 336 |
| GGC | AGT | GAG | CCA | TTG | TAT | GAC | GGA | TCA | AAA | CTT | GCG | GCA | CAG | 378 |
| GGA | GAA | GTC | ATT | GTC | GTT | ACA | TTG | AAC | TAT | CGG | CTG | GGG | CCG | 420 |
| TTT | GGC | TTT | TTG | CAC | TTG | TCT | TCG | TTT | GAT | GAG | GCG | TAT | TCC | 462 |
| GAT | AAC | CTT | GGG | CTT | TTA | GAC | CAA | GCC | GCC | GCG | CTG | AAA | TGG | 504 |
| GTG | CGG | GAG | AAT | ATC | TCA | GCG | TTT | GGC | GGT | GAT | CCC | GAT | AAC | 546 |
| GTA | ACA | GTA | TTT | GGA | GAA | TCC | GCC | GGC | GGC | ATG | AGC | ATT | GCC | 588 |
| GCG | CTG | CTC | GCT | ATG | CCT | GCG | GCA | AAA | GGC | CTG | TTC | CAG | AAA | 630 |
| GCG | ATC | ATG | GAA | AGC | GGC | GCT | TCC | CGA | ACA | ATG | ACA | AAA | GAA | 672 |
| CAA | GCG | GCA | AGC | ACT | GCG | GCT | GCC | TTT | TTA | CAG | GTC | CTT | GGG | 714 |
| ATT | AAT | GAG | AGC | CAG | CTG | GAC | AGA | TTG | CAT | ACT | GTA | GCA | GCG | 756 |
| GAA | GAT | TTG | CTT | AAA | GCG | GCC | GAT | CAG | CTT | CGG | ATT | GCA | GAA | 798 |
| AAA | GAA | AAT | ATC | TTT | CAG | CTG | TTC | TTC | CAG | CCC | GCC | CTT | GAT | 840 |
| CCG | AAA | ACG | CTG | CCT | GAA | GAA | CCA | GAA | AAA | TCG | ATC | GCA | GAA | 882 |
| GGG | GCT | GCT | TCC | GGC | ATT | CCG | CTA | TTG | ATT | GGA | ACA | ACC | CGT | 924 |
| GAT | GAA | GGA | TAT | TTA | TTT | ACC | CCG | GAT | TCA | GAC | GTT | CAT | | 966 |
| TCT | CAG | GAA | ACG | CTT | GAT | GCA | GCA | CTC | GAG | TAT | TTA | CTA | GGG | 1008 |
| AAG | CCG | CTG | GCA | GAG | AAA | GCT | GCC | GAT | TTG | TAT | CCG | CGT | TCT | 1050 |
| CTG | GAA | AGC | CAA | ATT | CAT | ATG | ATG | ACT | GAT | TTA | TTA | TTT | TGG | 1092 |
| CGC | CCT | GCC | GTC | GCC | TAT | GCA | TCC | GCA | CAG | TCT | CAT | TAC | GCC | 1134 |
| CCT | GTC | TGG | ATG | TAC | CGG | TTC | GAT | TGG | CAC | CCG | GAG | AAG | CCG | 1176 |
| CCG | TAC | AAT | AAA | GCG | TTT | CAC | GCA | TTA | GAG | CTT | CCT | TTT | GTC | 1218 |
| TTT | GGA | AAT | CTG | GAC | GGA | TTG | GAA | CGA | ATG | GCA | AAA | GCG | GAG | 1260 |
| ATT | ACG | GAT | GAG | GTG | AAA | CAG | CTT | TCT | CAC | ACG | ATA | CAA | TCC | 1302 |
| GCG | TGG | ATC | ACG | TTC | GCT | AAA | ACA | GGA | AAC | CCA | AGC | ACC | GAA | 1344 |
| GCT | GTG | AAT | TGG | CCG | GCG | TAT | CAT | GAA | GAA | ACG | AGA | GAG | ACG | 1386 |
| GTG | ATT | TTA | GAC | TCA | GAG | ATT | ACG | ATC | GAA | AAC | GAT | CCC | GAA | 1428 |
| TCT | GAA | AAA | AGG | CAG | AAG | CTA | TTC | CCT | TCA | AAA | GGA | GAA | TAA | 1470 | wherein A is a deoxyadenyl residue, G is a deoxyguanyl residue, C is a deoxycytidyl residue, and T is a thymidyl residue.

The amino acid sequence of the PNB esterase encoded by the DNA listed above is designated as SEQ ID NO: 2. This sequence is listed below from left to right in the amino-terminus to carboxy-terminus orientation.

| | | | | | | | | | | | | | | |
|---|---|---|---|---|---|---|---|---|---|---|---|---|---|---|
| Met 1 | Thr | His | Gln | Ile 5 | Val | Thr | Thr | Gln | Tyr 10 | Gly | Lys | Val | Lys | Gly 15 |
| Thr | Thr | Glu | Asn | Gly 20 | Val | His | Lys | Trp | Lys 25 | Gly | Ile | Pro | Tyr | Ala 30 |
| Lys | Pro | Pro | Val | Gly 35 | Gln | Trp | Arg | Phe | Lys 40 | Ala | Pro | Glu | Pro | Pro 45 |
| Glu | Val | Trp | Glu | Asp 50 | Val | Leu | Asp | Ala | Thr 55 | Ala | Tyr | Gly | Pro | Ile 60 |
| Cys | Pro | Gln | Pro | Ser 65 | Asp | Leu | Leu | Ser | Leu 70 | Ser | Tyr | Thr | Glu | Leu 75 |
| Pro | Arg | Gln | Ser | Glu 80 | Asp | Cys | Leu | Tyr | Val 85 | Asn | Val | Phe | Ala | Pro 90 |
| Asp | Thr | Pro | Ser | Gln 95 | Asn | Leu | Pro | Val | Met 100 | Val | Trp | Ile | His | Gly 105 |
| Gly | Ala | Phe | Tyr | Leu 110 | Gly | Ala | Gly | Ser | Glu 115 | Pro | Leu | Tyr | Asp | Gly 120 |
| Ser | Lys | Leu | Ala | Ala 125 | Gln | Gly | Glu | Val | Ile 130 | Val | Val | Thr | Leu | Asn 135 |
| Tyr | Arg | Leu | Gly | Pro 140 | Phe | Gly | Phe | Leu | His 145 | Leu | Ser | Ser | Phe | Asp 150 |
| Glu | Ala | Tyr | Ser | Asp 155 | Asn | Leu | Gly | Leu | Leu 160 | Asp | Gln | Ala | Ala | Ala 165 |
| Leu | Lys | Trp | Val | Arg 170 | Glu | Asn | Ile | Ser | Ala 175 | Phe | Gly | Gly | Asp | Pro 180 |
| Asp | Asn | Val | Thr | Val 185 | Phe | Gly | Glu | Ser | Ala 190 | Gly | Gly | Met | Ser | Ile 195 |
| Ala | Ala | Leu | Leu | Ala 200 | Met | Pro | Ala | Ala | Lys 205 | Gly | Leu | Phe | Gln | Lys 210 |
| Ala | Ile | Met | Glu | Ser 215 | Gly | Ala | Ser | Arg | Thr 220 | Met | Thr | Lys | Glu | Gln 225 |
| Ala | Ala | Ser | Thr | Ala 230 | Ala | Ala | Phe | Leu | Gln 235 | Val | Leu | Gly | Ile | Asn 240 |
| Glu | Ser | Gln | Leu | Asp 245 | Arg | Leu | His | Thr | Val 250 | Ala | Ala | Glu | Asp | Leu 255 |
| Leu | Lys | Ala | Ala | Asp 260 | Gln | Leu | Arg | Ile | Ala 265 | Glu | Lys | Glu | Asn | Ile 270 |
| Phe | Gln | Leu | Phe | Phe 275 | Gln | Pro | Ala | Leu | Asp 280 | Pro | Lys | Thr | Leu | Pro 285 |
| Glu | Glu | Pro | Glu | Lys 290 | Ser | Ile | Ala | Glu | Gly 295 | Ala | Ala | Ser | Gly | Ile 300 |
| Pro | Leu | Leu | Ile | Gly 305 | Thr | Thr | Arg | Asp | Glu 310 | Gly | Tyr | Leu | Phe | Phe 315 |
| Thr | Pro | Asp | Ser | Asp 320 | Val | His | Ser | Gln | Glu 325 | Thr | Leu | Asp | Ala | Ala 330 |
| Leu | Glu | Tyr | Leu | Leu 335 | Gly | Lys | Pro | Leu | Ala 340 | Glu | Lys | Ala | Ala | Asp 345 |
| Leu | Tyr | Pro | Arg | Ser 350 | Leu | Glu | Ser | Gln | Ile 355 | His | Met | Met | Thr | Asp 360 |
| Leu | Leu | Phe | Trp | Arg 365 | Pro | Ala | Val | Ala | Tyr 370 | Ala | Ser | Ala | Gln | Ser 375 |
| His | Tyr | Ala | Pro | Val 380 | Trp | Met | Tyr | Arg | Phe 385 | Asp | Trp | His | Pro | Glu 390 |
| Lys | Pro | Pro | Tyr | Asn 395 | Lys | Ala | Phe | His | Ala 400 | Leu | Glu | Leu | Pro | Phe 405 |
| Val | Phe | Gly | Asn | Leu 410 | Asp | Gly | Leu | Glu | Arg 415 | Met | Ala | Lys | Ala | Glu 420 |
| Ile | Thr | Asp | Glu | Val 425 | Lys | Gln | Leu | Ser | His 430 | Thr | Ile | Gln | Ser | Ala 435 |
| Trp | Ile | Thr | Phe | Ala 440 | Lys | Thr | Gly | Asn | Pro 445 | Ser | Thr | Glu | Ala | Val 450 |
| Asn | Trp | Pro | Ala | Tyr 455 | His | Glu | Glu | Thr | Arg 460 | Glu | Thr | Val | Ile | Leu 465 |
| Asp | Ser | Glu | Ile | Thr 470 | Ile | Glu | Asn | Asp | Pro 475 | Glu | Ser | Glu | Lys | Arg 480 |
| Gln | Lys | Leu | Phe | Pro 485 | Ser | Lys | Gly | Glu 489 | | | | | | | wherein Ala is an alanine residue, Arg is an arginine residue, Asn is an asparagine residue, Asp is an aspartic acid residue, Cys is a cysteine residue, Gln is a glutamine residue, Glu is a glutamic acid residue, Gly is a glycine residue, His is a histidine residue, Ile is an isoleucine residue, Leu is a leucine residue, Lys is a lysine residue, Met is a methionine residue, Phe is a phenylalanine residue, Pro is a proline residue, Ser is a serine residue, Thr is a threonine residue, Trp is a tryptophan residue, Tyr is a tyrosine residue, and Val is a valine residue.

The DNA sequence depicted above can be conventionally synthesized by the modified triester method using fully protected deoxyribonucleotide building blocks. Such synthetic methods are well known in the art and can be carried out in substantial accordance with the procedure of Itakura et al., 1977, *Science* 918:1056, and Crea et al., 1978, *Proc. Nat. Acad. Sci. USA* 75:5765. In addition, an especially preferred method is disclosed by Hsiung et al., 1983, *Nucleic*

*Acid Research* 11:3227, and Narang et al., 1980, *Methods in Enzymology* 68:90. In addition to the procedures referenced above, the DNA sequence can be synthesized using automated DNA synthesizers, such as the ABS (Applied Biosystems, 850 Lincoln Centre Drive, Foster City, Calif. 94404) 380A DNA Synthesizer. The DNA sequence can also be generated by the polymerase chain reaction. See, e.g., U.S. Pat. Nos. 4,800,159 and 4,683,202 and European Patent Publication No. 0258017, published Mar. 2, 1987.

The amino acid sequence of the PNB esterase depicted above can be encoded by a multitude of different DNA sequences because most of the amino acid residues are encoded by more that one DNA triplet. Because these alternate DNA sequences would encode the same amino acid sequence of this invention, the present invention further comprises these alternate DNA sequences.

As one of ordinary skill in the art will recognize, the present invention allows one to change the codons of the PNB esterase gene at will. Given the DNA sequence for the PNB esterase gene, procedures well known in the art can be used to generate mutant PNB esterase enzymes that vary from the natural enzyme at any number of amino acid residue positions. Such mutant enzymes would be encoded by mutant PNB esterase coding sequences, including sequences in which amino acid codons have been deleted from or inserted into the natural PNB esterase coding sequence. Such mutant enzymes are within the scope of the present invention, because even if one cannot absolutely predict whether a given mutation will destroy activity of the encoded PNB esterase, one need merely express the mutant sequence via the procedures provided herein to ascertain the effect on PNB esterase activity.

The present invention is not limited to the particular vectors exemplified herein. Instead, the present invention comprises DNA compounds that encode the PNB esterase activity of *Bacillus subtilis*. The DNA compounds of the present invention can be used to construct expression vectors that drive expression of esterase activity in any host cell in which the expression vector replicates or integrates and in which the promoter and translational activating sequence are functional.

Therefore, the present invention comprises any *Escherichia coli* plasmid or other vector that drives expression of PNB esterase activity in *E. coli*. The present invention comprises vectors that drive expression of PNB esterase activity and utilize a replicon functional in *E. coli*, such as, for example, a replicon from such plasmids as pBR322, pACYC184, F, ColV-K94, R1, R6-5, or R100. Nor is the present invention solely limited to plasmid vectors, for the present invention also comprises other vectors that express PNB esterase activity and utilize integration or viral replication to provide for replication and maintenance in the host cell.

The present invention is not limited to a particular promoter and translational activating sequence to drive expression of the PNB esterase activity-encoding DNA. The present invention comprises the use of any promoter and translational activating sequence that function in *Escherichia coli* and are used to express PNB esterase activity in *E. coli*. Many promoter and translational activating sequences functional in *E. coli* are known and are suitable for driving expression of esterase activity in *E. coli*. Such transcriptional and translational activating sequences include, but are not limited to, the lpp, lac, trp, tac, λpL, and λpR promoter and translational activating sequences. In addition, modified bacteriophage lambda promoters such as those disclosed in U.S. patent application Ser. No. 07/739,280, which is incorporated herein by reference, are useful in the present invention.

In addition, transcriptional and translational activating sequences from other organisms can be ligated to the present PNB esterase-activity-encoding DNA compounds to form expression vectors that drive expression of PNB esterase activity in the host cells in which the activating sequence functions. Although *Escherichia coli* is the host best suited for PNB esterase production and subsequent purification for in vitro use, vectors that drive expression of PNB esterase activity in host cells other than *E. coli* are also useful.

A vector that will increase the intracellular concentration of PNB esterase activity of a given host cell into which the vector is transformed requires the following elements: 1) a PNB esterase activity-encoding DNA compound of the present invention; and 2) a promoter and translational activating sequence that not only function in the host cell to be transformed, but also are positioned in the correct orientation and position to drive expression of the PNB esterase activity-encoding DNA. Of course, stable transformants can only be obtained if the vector replicates, either as an extrachromosomal element or integrated in the genomic DNA, in the host cell. Thus, a preferred vector contains sequences that specifically direct replication or integration of the vector in the host cell. However, the presence of such specific replication or integration sequences is not absolutely required, as non-specific integration may occur when DNA is introduced into a host cell. An PNB esterase expression vector could also comprise an antibiotic resistance-conferring gene or some other element that provides a means of selecting for host cells which contain the vector, but such selectable elements may neither be necessary nor desired when the vector integrates into the chromosomal DNA of the host cell.

By providing the coding sequence of the PNB esterase gene of *Bacillus subtilis*, the present invention provides PNB esterase expression vectors for any organism susceptible to transformation. The *Escherichia coli* PNB esterase expression vectors described herein illustrate the wide variety of expression vectors of the present invention. However, many of the preferred vectors of the invention are designed to drive expression of the PNB esterase.

The following Examples are intended to assist in the further understanding of the invention. Particular materials employed, species, and conditions are intended to be further illustrative of the invention and not limiting the reasonable scope thereof. Procedures for the manipulation and analysis of DNA were performed essentially as described by Sambrook et al., 1989, *Molecular Cloning: a Laboratory Manual*, Cold Spring Harbor Laboratory Press, Cold Spring Harbor, N.Y.

Conditions for restriction enzyme reactions were those recommended by the manufacturers (Boehringer Mannheim (BM), Indianapolis, Ind.; New England Biolabs (NEB), Beverly, Mass.; Bethesda Research Labs (BRL), Gaithersburg, Md.).

EXAMPLE 1

Isolation of PNB Esterase Gene (pnbA) from a Genomic Library of *Bacillus subtilis* (NRRL B8079) DNA A. Description and Genotypes of Strains

*Bacillus subtilis* strain NRRL B8079 was isolated in a screen designed to identify microorganisms capable of removing the para-nitrobenzyl ester from cephalosporins (Brannon et al., *J. Antibiotics* XXIX No. 2:121–124 1976). *B. subtilis* NRRL B-8079 has been deposited in the permanent culture collection of the Northern Regional Research Laboratory (NRRL), United States Department of Agriculture Service, Peoria, Ill. 61604, and is available under accession number B-8079. *Escherichia coli* K12 DH5α™ (MAX Efficiency DH5α™ Competent Cells; GIBCO BRL, Gaithersburg, Md.), which is a recA⁻ strain that has been developed to be highly transformable and provide a stable environment for maintenance of plasmids, was used as host strain for the *B. subtilis* strain NRRL B8079 genomic library (see Example 1J). The recA+ *E. coli* K12 strain RV308, was used for high-level expression of the cloned PNB esterase gene and is a preferred host for expression of heterologous proteins in *E. coli* on an industrial scale. *E. coli* K12 RV308 has been deposited with the NRRL and is available under accession number B-15624. *E. coli* W ATCC 11105 can also be used as host for expression of heterologous proteins. This host strain can be obtained from the American Type Culture Collection (ATCC), Rockville, Md. 20852, under accession number ATCC 11105.

B. Cultivation of Strains

Trypticase®-Soy broth (TSB; Becton Dickinson Microbiology Systems) and Luria broth (L-broth; 10 g Difco Bacto-Tryptone®, 10 g NaCl, and 5 g yeast extract per liter) were used as growth medium for liquid cultures. Cultures on solid medium were grown on L-broth supplemented with 2% w/v agar (L-agar). Antibiotics were added to medium where necessary, at the following concentrations: 25 ampicillin (50 µg/ml), and tetracycline (5 µg/ml). 5-bromo-4-chloro-3-indolyl-D-galactoside (X-gal; Sigma Chemical Co., St. Louis, Mo. 63178) was added to media at 20 µg/ml to detect β-galactosidase activity.

C. Transformation of *Escherichia coli* K12 DH5α, *E. coli* K12 RV308, and *E. coli* W ATCC 1105

*Escherichia coli* K12 DH5α competent cells were obtained from BRL and were transformed using the manufacturer's protocol. Alternatively, 50 ml cultures of *Escherichia coli* strains DH5α, RV308 or ATCC 11105 were grown in L-broth to an $OD_{590}$ of approximately 0.5 absorbance units, and the cells were collected by centrifugation. The cell pellet was resuspended in 25 ml of cold 100 mM $CaCl_2$ and incubated on ice for 25 minutes. The cells were collected by centrifugation, resuspended in 2.5 ml of cold 100 mM $CaCl_2$ and incubated on ice overnight. Competent cells were used directly or stored at −70° C. until ready for use in transformations.

To transform competent *Escherichia coli* cells, one hundred microliters of the competent cell suspension were removed from storage at −70° C. and allowed to thaw on ice. Cells were gently mixed with five microliters of a solution of plasmid DNA (1 ng/µl) in a polypropylene tube, and the resulting solution was incubated on ice for 30 minutes. The tube was transferred to a 42° C. water bath and incubated without shaking for 45 seconds. After this heat-shock treatment, the tube was placed on ice for 2 minutes. The tube was then removed from the ice and 0.9 ml of S.O.C. medium (2% Bacto-Tryptone®; 0.5% yeast extract; 10 mM NaCl; 2.5 mM KCl; 10 mM $MgCl_2$; 10 mM $MgSO_4$; and 20 mM glucose), pre-incubated to room temperature, was added. The cell suspension was then shaken at 225 rpm for 1 hour at 37° C. and aliquots were plated on L-agar containing ampicillin. Putative transformants were picked from plates after incubation at 37° C., and their identity was confirmed by sizing their plasmid DNA using horizontal gel electrophoresis (Sambrook et al., 1989). Plasmid DNA from selected clones was characterized by restriction enzyme analysis.

D. Plasmid DNA isolation

Plasmid DNA was isolated from *Escherichia coli* strains using a standard alkaline-SDS procedure (Sambrook et al., 1989). Alternatively, plasmid DNA was isolated as follows. A portion of a transformant colony growing on L-agar containing 50 mg/ml ampicillin was transferred to one liter of L-broth containing 50 mg/ml ampicillin and incubated in an air-shaker at 37° C. for about 16 hours. Cells were harvested in 500 ml bottles in a Beckmann JA-10 rotor (Beckman Instruments Inc., Fullerton, Calif. 92634) at 8000 rpm for 10 minutes at 4° C. The cell pellet was washed with TE, pH 8.0 (10 mM Tris-HCl, 1 mM ethylenediamine tetraacetic acid (EDTA)), collected by centrifugation, and resuspended in 50 mM Tris-HCl, pH 8.0, 25% sucrose to a total volume of 10 ml. One milliliter of 20 mg/ml lysozyme (Sigma Chemical Co., St. Louis, Mo.) in 25 mM Tris-HCl, pH 8.0, was added with stirring, and the mixture was incubated on ice for 30 minutes. Four milliliters of 200 mM EDTA was added, with subsequent incubation on ice for 10 minutes, followed by the addition of 15 ml of Brij/DOC lysing solution (1% Brij 58; 0.4% deoxycholate; 50 mM Tris-HCl, pH 8.0; 60 mM EDTA). Tubes were gently inverted to mix, and incubated on ice for 15–30 minutes. Cell debris was removed by centrifugation at 18,000 rpm in a Beckman JA-20 rotor for 1 hour. Supernatant was decanted yielding approximately 30 ml, to which 150 ml of 10 mg/ml RNAse A (Sigma Chemical Co.) was added. After a 1 hour incubation at 37° C., 150 ml of 10 mg/ml Proteinase K (Boehringer Mannheim) was added followed by another 1 hour incubation at 37° C. DNA was precipitated by the addition of 1/10 volume of 3M sodium acetate, pH 7.0, followed by 3× volumes of ice cold absolute ethanol. DNA was recovered by centrifugation in a Beckman JA-14 rotor (Beckman Instruments Inc., Fullerton, Calif. 92634) at 8,000 rpm for 30 minutes. The air dried pellet was resuspended in TE, pH 8.0, to a total volume of 9 ml, to which was added 9 g of cesium chloride (Boehringer Mannheim) and 0.5 ml of 10 mg/ml ethidium bromide. The resulting solution was loaded into two 5.1 ml Quik-seal tubes (Beckman Instruments Inc.) and centrifuged at 65,000 rpm in a Beckman VTi65.2 ultracentrifuge rotor for 6 hours. The plasmid band was visualized under ultraviolet light and was removed by syringe. The resulting DNA solution was extracted with salt-saturated isopropanol to remove the ethidium bromide, and dialyzed 16 hours against 1000× volumes TE, pH 8.0. DNA solutions were stored at −20° C. until needed.

E. Polymerase Chain Reaction (PCR) Amplifications

Polymerase chain reactions were performed using a DNA Thermal Cycler™ and the Gene-Amp™ reagent kit (Perkin-Elmer Cetus, Norwalk., Conn. 06859) according to the instructions of the manufacturer. Thirty cycles of amplification were performed, with each cycle consisting of the following incubations: 1 min at 93° C., followed by 2 min at 40° C., followed by 4 min at 72° C. Syntheses were completed by incubation at 72° C. for 10 min.

F. Nucleotide Sequence Analysis

Supercoiled plasmid DNA templates for sequencing were purified from alkaline lysates of *Escherichia coli* cultures on Qiagen DNA binding columns (Qiagen, Inc., Chatsworth, Calif.) according to protocols provided by the manufacturer. Dideoxynucleotide chain-termination sequencing reactions were performed according to a cycle sequencing protocol (Applied Biosystems, Inc. (ABI), Foster City, Calif. 94404) with fluorescent dye-labelled dideoxynucleotides, supercoiled plasmid templates, and sequence specific oligonucleotide primers. Sequence reactions were analyzed on an ABI model 373A automated DNA sequencer. Nucleotide sequences were compiled, edited, and analyzed with the GCG computer programs of Devereux et al., 1985, *Nucleic Acids Res.* 12:387–395.

G. Synthesis and End-labelling of Oligonucleotide Probes

The amino-terminal sequence of PNB esterase purified from *Bacillus subtilis* NRRL B8079 (purified by the method of Example 7) was obtained by subjecting 25 picomoles of purified PNB esterase [ca. MW=54,000], specific activity ca. 2.2 U/mg (based on hydrolysis of loracarbef PNB ester to corresponding free acid), to analysis in an automated gas phase sequenator (Hewick et al., 1981, *J. Biol. Chem.* 256:7990; Hunkapiller & Hood, 1978, *Biochemistry* 17:2124). The amino acid sequence of the amino-terminal end of PNB esterase is: Met Thr His Gln Ile Val Thr Thr Tyr Gly Lys Lys Val Lys Gly Thr Gln Glu Asn Gly Val His (SEQ ID NO. 3).

Based on this sequence and the known codon usage for *Bacillus subtilis*, (Harwood et al., *Molecular Biological Methods for Bacillus*, John Wiley and Sons Ltd., West Sussex, England (1990)) two oligonucleotide probes were synthesized on an Applied Biosystems Inc. model 380B DNA synthesizer using β-cyanoethyl phosphoramidite chemistry, according to the manufacturer's instructions. These oligonucleotide probes, called PNB1 and PNB2, are presented below from left to right in the 5' to 3' orientation:

PNB1—ATGACACATC AAATTGTCAC AACATATGGC AAAAAAGTCA A (SEQ ID NO. 4)

PNB2—TATGGCAAAA AAGTCAAAGG CACACAAGAA AATGGCGTCC A (SEQ ID NO. 5)

The single stranded DNA segments were first column-purified (Oligonucleotide Purification Cartridges; Applied Biosystems, Inc.) and then end-labelled as follows. Ten picomoles of each probe were added to a 20 µl reaction mixture containing 12 µl [λ-32P] adenosine triphosphate (ATP; 5000 Ci/ml) and 8 units of T4 polynucleotide kinase in kinase buffer (50 mM Tris-HCl, pH 7.6, 10 mM $MgCl_2$). Following a 35 min reaction at 37° C., and a 5 minute incubation at 70° C. to inactivate the kinase, the unincorporated [λ32p] ATP was removed from the reaction mixture using a Sephadex G-50 Nick Column (Pharmacia Inc, Piscataway, N.J. 08854).

H. Isolation of Genomic DNA from *Bacillus subtilis* NRRL B8079

Total DNA was isolated from a two liter culture of *Bacillus subtilis* NRRL B8079 grown to mid-logarithmic phase in TSB at 25° C. for 16 hr. Cells were harvested by centrifugation and resuspended in 20 ml of buffer (50 mM Tris-HCl, pH 8.0, 50 mM EDTA). Lysis of cells was accomplished in two steps by: (i) addition of 1 mg/ml lysozyme (from egg white; Calbiochem, La Jolla, Calif.) and incubation of the suspension for 20 min at 37° C., and (ii) addition of 4 ml of lysing buffer (0.5% sodium dodecyl sulfate [SDS], 50 mM Tris pH 7.5, 0.4M EDTA, 1 mg/ml Proteinase K) and incubation at 50° C. for 30 min. The DNA was purified by two phenol extractions followed by one chloroform extraction, and then recovered by precipitation with ethanol and spooling on a glass rod. RNA was removed from the preparation by gently resuspending the DNA in 40 mM Tris-HCl buffer, pH 7.5, containing 1 mM EDTA and 0.2 mg/ml ribonuclease (from bovine pancreas; Sigma Chemical Co.) and then incubating the preparation at 25° C. for 30 min. Further purification was accomplished by re-extraction with phenol and chloroform, precipitation with ethanol, and resuspension in TE, pH 7.5.

I. Southern Hybridizations of EcoRI Restriction Fragments Using Oligonucleotide Probes Genomic DNA from *Bacillus subtilis* NRRL B8079 was digested with EcoRI and subjected to electrophoresis on a 1% agarose-TBE gel (Sambrook et al., 1989). The size-fractionated DNA was then transferred to Hybond-N+ nylon membranes (Amersham, Arlington Heights, Ill., U.S.A.) by Southern blotting (Sambrook et al., 1989), and cross-linked to the matrix by treatment with ultraviolet light for 5 min. After pre-hybridization of the DNA at 70° C. for 1–2 hr in hybridization buffer containing 6× SSC (1× SSC, pH 7.0, contains 0.15M sodium chloride, 0.015M sodium citrate), 5× Denhardt's solution (1× Denhardt's solution contains 0.2 g/l Ficoll 400, 0.2 g/l polyvinylpyrollidone and 0.2 g/l bovine serum albumin [Fraction V]), 0.25% SDS, and 20 µg/ml calf thymus DNA, fragmented by treatment with ultrasound. Fresh hybridization buffer containing [$^{32}P$]-labelled oligonucleotide (prepared as described in Example 1G) was then added to produce a final probe concentration of 0.5 pmoles/ml. The temperature of the incubation mixture was allowed to fall to 45° C. during overnight incubation. The membranes were then washed using conditions of stringency that had been optimized for each probe. Membranes hybridized to PNB1 were washed for 25 min, three times in succession, at 45° C. in 4× SSC, 0.25% SDS. Membranes hybridized to PNB2 were washed similarly, with 0.5× SSC, 0.25% SDS. After washing, the membranes were dried at room temperature and exposed to film.

Using the above procedure, a band representing EcoRI fragments of approximately 6 kb in size was shown to hybridize to probes PNB1 and PNB2.

J. Construction of an Enriched Library of EcoRI DNA Fragments and Isolation of pNBE1

*Bacillus subtilis* NRRL B8079 genomic DNA was completely digested with EcoRI and subjected to electrophoresis in a horizontal 1.2% agarose gel (in 1× TAE buffer containing 40 mM Tris-acetate, 1 mM EDTA; 2 V/cm) for 16 hr. The gel was stained in a dilute (1 mg/ml) ethidium bromide solution and the DNA bands visualized under long-wave ultraviolet light. A slice was removed from the region of the gel that corresponded to DNA of approximately 6 kb in size, and that spanned the band that had previously been shown to hybridize to PNB1 and PNB2. Elution of the DNA fragment from the gel slice was performed according to the protocol of Sambrook et al. (1989), with minor adjustments. Briefly, the gel slice was put into a dialysis bag with 200 µl 0.2× TAE buffer, sealed with clips, and electrophoresed in 0.2× TAE buffer for about 3 hours. The contents of the dialysis bag, including a 400 µl wash with 0.2× TAE, were mixed with 2.4 ml of low salt buffer (0.2M NaCl; 20 mM Tris-HCl, pH 7.5; 1.0 mM EDTA) and loaded onto an ELUTIP-d column (Schleicher & Schuell, Keene, N.H.) prepared according to the manufacturer's protocol. After washing with low salt buffer the DNA was eluted from the column with two 400 µl volumes of high salt buffer (1.0M NaCl; 20 mM Tris-HCl, pH 7.5; 1.0 mM EDTA) and precipitated by addition of 800 µl of ice-cold absolute ethanol followed by centrifugation at 14,000 rpm in an Eppendorf 5415C microfuge for 40 minutes. The two air-dried pellets were combined by dissolving in 20 ml TE, pH 7.5, and the solutions were stored at −20° C. until ligation. The fragments were ligated into the vector pUC19 (Gibco BRL, Gaithersburg, Md.) which was pre-treated by digestion with EcoRI followed by removal of the 5' phosphates using calf intestinal alkaline phosphatase (Calbiochem; La Jolla, Calif.).

The resulting plasmids were used to transform competent *Escherichia coli* K12 DH5α cells, which were then plated onto L-agar plates containing ampicillin and X-Gal. Use of plasmid pUC19 as a vector allowed the specific selection of clones containing insert DNA using blue/white selection.

Transformants containing only the pUC19 vector, which includes that portion of the lacZ gene that codes for the α-peptide of β-galactosidase, produce active enzyme, detected by cleavage of X-Gal to produce a blue color. In contrast, isolates containing an insert at the EcoRI site disrupt the reading frame of the α-peptide, and are unable to convert the X-Gal, and thus remain white on media containing X-Gal. More than one hundred white, ampicillin-resistant colonies were selected and replated on the same agar to test phenotypic stability.

Plasmid DNA was isolated from white colonies and analyzed by gel electrophoresis. Seven colonies containing plasmid DNA of the required 9 kb size (2.686 kb pUC19 DNA plus approximately 6 kb insert DNA) were selected for further study. When tested by Southern hybridizations, using the PNB2 probe, one plasmid, pNBE1, gave a strong hybridization signal. Digestion of plasmid pNBE1 with EcoRI yielded two fragments of the predicted size: one corresponding to linearized pUC19 (2.686 kb), and the other, approximately 6 kb in size, corresponding to the insert fragment.

K. Demonstration of the Direction of Transcription of pnbA on Plasmid pNBE1

Two PCR amplifications using pNBE1 were performed to determine the direction of transcription of pnbA, relative to the lacZ gene of pUC19, and the approximate position of the ATG transcription start site in the insert. The first amplification used the PNB2 oligonucleotide probe and the forward (−20) M13 DNA sequencing primer (New England BioLabs). The second amplification also used PNB2, but the second primer was the reverse (−24) M13 sequencing primer. Results showed that only the reaction with the (−20) forward sequencing primer generated an amplified fragment. The size of the amplified fragment was determined to be 2.0 kb. Therefore, the ATG start site of pnbA is located approximately 41 kilobase pairs (kb) downstream of the start of the multi-cloning site of pUC19, and is transcribed in the same direction as the lacZ gene.

L. Verification of a Functional pnbA Gene

To determine whether the entire pnbA gene was present on pNBE1 and capable of being expressed in *Escherichia coli*, extracts of *E. coli* K12 DH5α cells transformed with plasmid pNBE1 were assayed for esterase activity. Cell extracts were prepared from approximately 75 ml of a culture grown to mid-logarithmic phase in L-broth. Cells were collected by centrifugation for 10 min at 8,000 rpm, washed in 10 mM sodium phosphate buffer, pH 7.0, and recentrifuged. The cell pellet was resuspended (1 g cells/4 ml buffer) and disrupted by exposure to four 30 second bursts of ultrasound (Sonicator™ Cell Disruptor Model W185F, Heat Systems-Ultrasonics Inc., Plainview, N.Y.). Cell debris was removed by centrifugation in a microfuge for 20 min at maximum speed. Because purified PNB esterase catalyzes the cleavage of p-nitrophenyl acetate, in addition to p-nitrobenzyl esters of β-lactam antibiotics, this reaction could conveniently be used for monitoring the formation of p-nitrophenol spectrophotometrically. The reaction mixture contained 400 µl of 0.5M p-nitrophenyl acetate (in 1:99 v/v acetonitrile/water), 600 µl of 167 mM Tris-HCl, pH 7.0, and 1–20 µl of cell free extract. Formation of p-nitrophenol was measured spectrophotometrically by monitoring the increase in $OD_{405}$ using a Gilford Response II spectrophotometer. Alternatively, enzyme activity could be demonstrated qualitatively using whole cells by adding a portion of a colony to the reaction mixture using a toothpick. Assay of both whole cells and cell free extracts using these procedures demonstrated that plasmid pNBE1 contained an intact pnbA gene, and that the gene was expressed to produce active enzyme. No significant activity was detected in *Escherichia coli* K12 DH5α cells without plasmid, or with *E. coli* K12 DH5α cells carrying other non-hybridizing plasmids from the genomic library.

M. Subcloning of the pnbA Gene

With the information obtained from the PCR experiment described in Example 1K, and results from single and double restriction enzyme digestions of pNBE1, it was possible to construct a preliminary physical map of the 6.0 kb EcoRI fragment. A restriction enzyme and function map of plasmid pNBE1 is presented in FIG. 1. A series of subclones of pNBE1 were then made by partial digestion of the plasmid with HpaII, followed by complete digestion with EcoRI, and ligation of the resulting HpaII-EcoRI fragments to pUC19 digested with AccI-EcoRI. The HpaII site of the insert and the AccI site of pUC19 were not regenerated by this ligation. The resulting plasmids were then transformed into *Escherichia coli* K12 DH5α cells, and ampicillin-resistant colonies were selected and tested for esterase activity. Plasmid DNA was isolated from a number of positive clones and analyzed to determine the size of the HpaII-EcoRI inserts. The smallest insert that coded for active enzyme was 2.3 kb. The plasmid vector was designated pNBHpE2.3.

An additional subcloning experiment was performed which indicated that the SalI-EcoRI fragment at the distal end of the 2.3 kb insert was not required for a functional pnbA gene. pNBHpE2.3 was first digested with HindIII and SalI, ligated to pUC19 digested with HindIII and SalI, and then transformed into *Escherichia coli* K12 DH5α cells. The plasmid from this construction, designated pNBH3S1.9, contained a 1.9 kb HpaII-SalI insert, and coded for active PNB esterase protein. The insert DNA from this plasmid was subcloned into pBluescript SK(−) (Stratagene, La Jolla, Calif.) and analyzed to determine the nucleotide sequence. The coding sequence of the PNB esterase gene from *Bacillus subtilis* is presented in the Sequence Listing as SEQ. ID. NO. 1.

EXAMPLE 2

High Level Expression of the pnbA Gene in *Escherichia coli*

Figure 2:
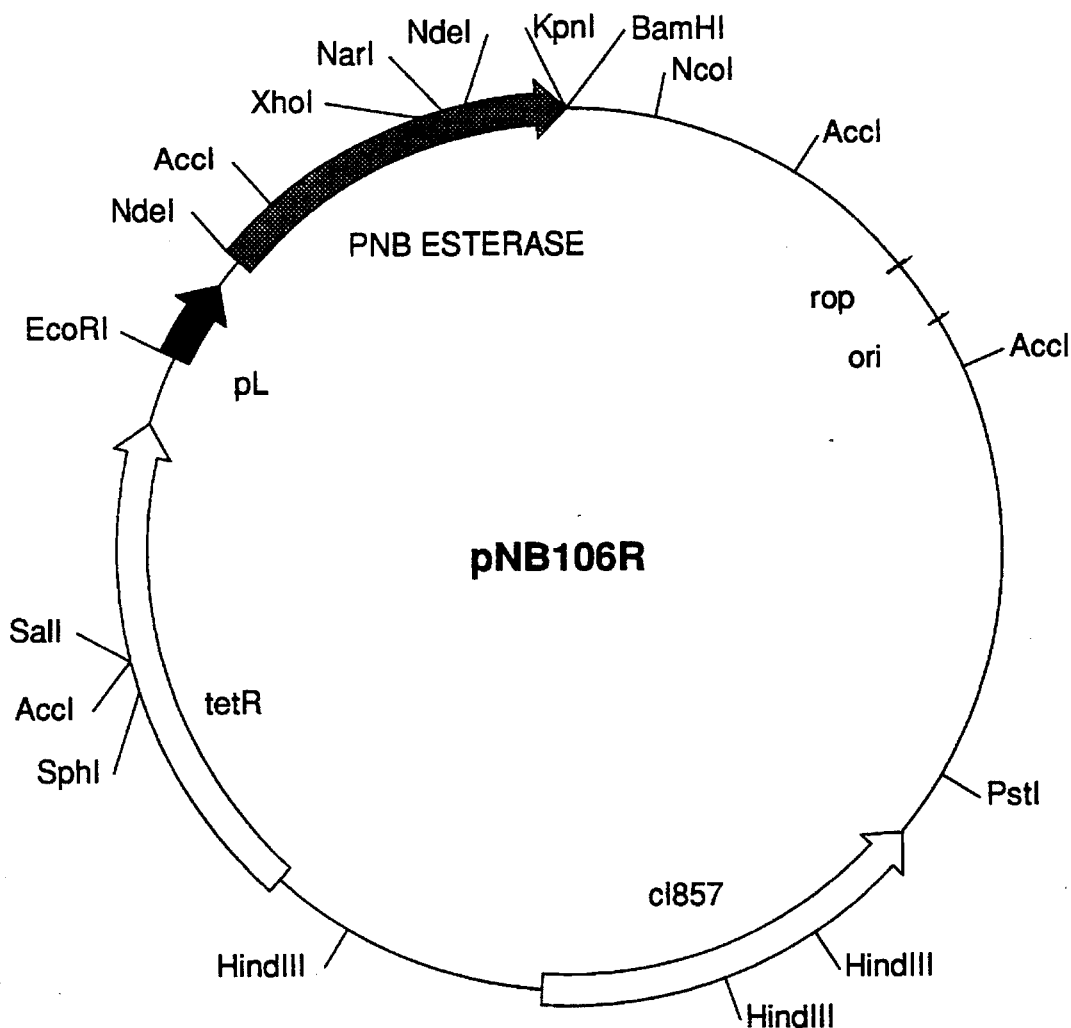
FIG. 2 is a restriction enzyme site and function map of plasmid pNB106R.
Figure 3:
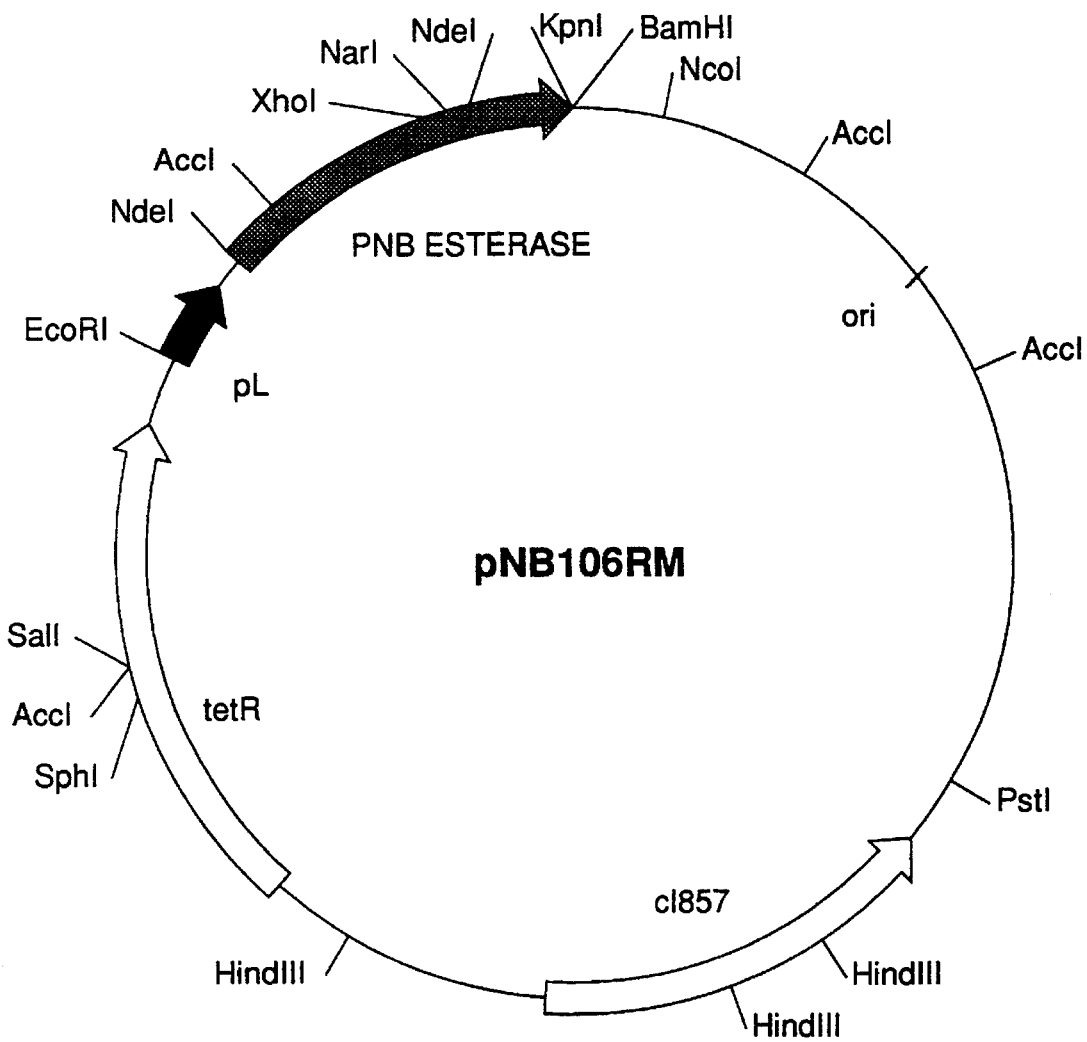
FIG. 3 is a restriction enzyme site and function map of plasmid pNB106RM.

Expression of the cloned PNB esterase gene in *Escherichia coli* was improved by construction of vectors pNB106R and pNB106RM. Plasmid pNB106R contains a functional rop gene, responsible for control of plasmid copy number (Cesareni et al., 1982, *Proc. Natl. Acad. Sci. USA* 79:6313). A restriction enzyme and function map of plasmid pNB106R is presented in FIG. 2. Plasmid pNB106RM, which lacks the rop gene, was derived from pNB106 to determine the effect of plasmid copy number upon expression of the pnbA gene. A restriction enzyme and function map of plasmid pNB106RM is presented in FIG. 3.

A. Construction of *Escherichia coli* K12 DH5α/pNB106R, *E. coli* K12 RV308/pNB106R and *E. coli* W ATCC 11105/pNB106R Plasmid pNB106R was generated by subcloning the 1.9 kb DNA fragment from plasmid pNBH3S1.9 into the temperature inducible high level expression vector pHKY593 to provide temperature inducible expression of a heterologous gene from a modified bacteriophage lambda pL promoter. *E. coli* RV308/pHKY593 was deposited with the NRRL on Aug. 5, 1993, and is available under accession number B-21127. The plasmid contains two regions of DNA of particular importance: (i) a sequence derived from pBR322 which allows replication and maintenance of the plasmid in

*Escherichia coli,* and in which the ampicillin resistance gene of pBR322 is replaced by a lambda cI857 repressor gene; and (ii) a sequence in which a modified lambda promoter, pL106 (U.S. patent application Ser. No. 07/739,280), situated downstream of the tetracycline resistance gene, is immediately adjacent to the open reading frame (ORF) of a kanamycin resistance gene. The promoter controls transcription of that ORF via an two cistron assembly (Schoner et al., 1990, *Methods in Enzymology* 185:94). Plasmid pHKY593 was constructed so that the open reading frame of the kanamycin resistance gene can easily be removed by digestion with NdeI and BamHI. Any ORF with an NdeI restriction site at its ATG transcriptional start codon, and a BamHI compatible restriction site downstream from its potential transcription termination sequences, can be inserted into pHKY593. The resulting inserted ORF will then be aligned correctly for expression from the pL promoter.

Because the cloned 1.9 kb *Bacillus subtilis* DNA did not contain an NdeI site at the desired location, a strategy was developed to introduce one at the ATG transcription start site of the pnbA ORF. The strategy involved separate constructions to generate amino-terminal and carboxy-terminal fragments of the pnbA gene, followed by ligation of the two fragments to a third fragment, obtained from the pHKY593 vector. Construction of the three fragments was accomplished as follows:

i) Amino-terminal Fragment

A 261 bp fragment coding for the amino-terminus of PNB esterase, containing an NdeI site adjacent and 5' to the ATG transcription start site, was synthesized using PCR technology (see Example 1E). The PCR amplification was performed using the following two primers listed from left to right in the 5' to 3' orientation:

PNBNDE1—AAAAAGGGAG AGAACCATAT GACT-CATCAA ATAG (SEQ ID NO.6); PNB5—TTGA-CATACA AGCAATCCTC (SEQ ID NO. 7).

The PNBNDE1 sequence underlined above represents the NdeI restriction site. The first three bases of the primer were not matched to the cloned PNB esterase gene. The other primer, PNB5, anneals approximately 25 bp downstream from the AccI site located 215 bp downstream from the ATG start site. The 261 bp fragment that resulted from the amplification was treated with Proteinase K (protease Type XXVIII, from *Tritirachium album*) according to the procedure described by Crowe et al., 1991, *Nuc. Acid Res.* 19:184, with minor modifications. The fragment was subsequently digested with NdeI and AccI, phenol extracted and ethanol precipitated by standard methods to generate the 180 bp fragment used in the ligation reaction presented below, ii) Carboxy-terminal Fragment Because the construction strategy required use of the AccI site internal to the ORF to splice the amino-terminal and carboxy-terminal fragments it was necessary to eliminate the other AccI site (SalI/AccI) on the 1.9 kb fragment. This was accomplished in two steps: (i) digestion of pNBH3S1.9 with HindIII and SalI to release the ORF fragment; and (ii) ligation of the released fragment to pBluescript SK(–) that had been digested with HindIII and XhoI. Insertion of the SalI/AccI site of the 1.9 kb fragment into the XhoI site of pBluescript SK(–), eliminated all three sites. Transformation of the ligation mixture into *Escherichia coli* K12 DH5α, followed by screening of putative clones and confirmation of structures by restriction digests, resulted in the isolation of pNBH3(SX)sk, which has only one AccI site, located in the ORF. Another construction was needed to introduce a BamHI site at the carboxy-terminus. This was accomplished by digestion of pNBH3(SX)sk with EcoRI and KpnI, to release the ORF fragment, followed by ligation of this fragment into pUC19, also digested with EcoRI and KpnI. Transformation of the ligation mixture into DH5α cells, followed by selection and analysis of clones, resulted in the isolation of plasmid pNBEKuc, which contained a single AccI site in the ORF, and an appropriately positioned BamHI site downstream from the carboxy-terminus.

iii) Vector Fragment from pHKY593

Vector for the three piece ligation reaction presented below was prepared by digestion of pHKY593 with NdeI and BamHI to remove the kanamycin resistance gene, and gel isolation of the large restriction fragment.

A three piece ligation was performed involving the NdeI-AccI digested PCR fragment (180 bp), the AccI-BamHI fragment of pNBEKuc (1.7 kb), and the NdeI-BamHI fragment of pHKY593 (6 kb). This produced plasmid vector pNB106R, containing the entire pnbA ORF under control of the temperature inducible lambda pL synthetic promoter. The resulting DNA was transformed into host strain *Escherichia coli* K12 DH5α. Plasmid pNB106R was subsequently transformed into host cells *E. coli* K12 RV308 and *E. coli* W ATCC 11105.

EXAMPLE 3

Construction of *Escherichia coli* K12 DH5α/pNB106RM, *E. coli* K12 RV308/pNB106RM and *E. coli* W ATCC 11105/pNB106RM To construct a version of pNB106R without the rop gene (rop⁻), the plasmids PNB106R and pHKY389 (rop⁻) were both digested with SphI and NcoI. *Escherichia coli* K12 RV308/pHKY389 was deposited with the NRRL and is available under accession number B-21012. The ~4.5 kb SphI-NcoI fragment from pHKY389, and the ~3 kb SphI-NcoI fragment from pNB106R were gel isolated following electrophoresis using low melting agarose. These fragments were ligated using T4 DNA ligase and standard reaction conditions at 37° C. for 4 hr. Competent *E. coli* K12 DH5α cells were transformed and plated on L-agar containing tetracycline. Selected clones were screened for the expected AccI restriction enzyme pattern, and a strain carrying plasmid pNB106RM was thereby identified. Plasmid pNB106RM was subsequently transformed into strains *E. coli* K12 DH5α, *E. coli* K12 RV308, and *E. coli* W ATCC 11105 using the procedure described in Example 1.

EXAMPLE 4

Synthesis of PNB Esterase in *Escherichia coli* K12 DH5α, *E. coli* K12 RV308 and *E. coli* W ATCC 11105 Transformed with pNB106R or pNB106RM Synthesis of PNB esterase by cultures of *Escherichia coli* K12 DH5α, *E. coli* K12 RV308 and *E. coli* W ATCC 11105 transformed with plasmid pNB106R or pNB106RM was induced as follows. A frozen stock culture of the strain was used to inoculate L-broth containing 5 μg/ml tetracycline. After 16 hr growth at 30° C., cells were subcultured (4% v/v) into fresh L-broth plus tetracycline and grown to mid-logarithmic phase. Induction of enzyme synthesis was accomplished by raising the temperature of the culture to 40° C. The kinetics of PNB esterase synthesis was measured by sampling the culture periodically and assaying enzyme activity in cell free extracts as described in Example 1L. Cell-free extracts were also analyzed by SDS-polyacrylamide gel electrophoresis (SDS-PAGE) to allow the relative increase in the amount of PNB esterase protein to be monitored.

EXAMPLE 5

Purification of PNB Esterase from Recombinant *Escherichia coli* Strains

The PNB esterase was purified from *Escherichia coli* K12 DH5α/pNB106R by the procedure outlined in Table 1. This procedure can be compared to the purification from Bacillus, presented in Example 7 and outlined in Table 2. It will be noted that in the latter case eight (8) steps were required and 2.6 mg of pure enzyme was obtained from 130,000 mg of crude protein, whereas from the recombinant *Escherichia coli* strain 10 mg of pure enzyme was obtained from only 200 mg of crude protein using only 6 steps. Thus, the simpler process of purification, using recombinant *E. coli* as the source, was 3250 times more efficient than the old more complex purification process where the natural producer, *Bacillus subtilis*, was used as enzyme source.

Because the new purification procedure with recombinant *Escherichia coli* as the source of enzyme is considerably simpler, it would be less expensive to apply at large scale than the purification procedure needed for the same enzyme obtained from *B. subtilis*. This is a direct result of the significantly increased amount of PNB esterase obtained in the recombinant *E. coli* strain (ca. 3250 fold per unit crude protein).

The PNB esterase purified from recombinant *Escherichia coli* was compared to the native enzyme by molecular weight, Western blot analysis, and substrate specificity. Measurements of molecular weight gave values of 54,000 for enzyme from the two sources, and identical precipitin bands were obtained when the two enzyme preparations were tested using antibody prepared against native purified esterase. Both enzymes hydrolyzed cefaclor PNB ester, cefaclor nucleus PNB ester, loracarbef PNB ester, and loracarbef nucleus PNB ester. The native PNB esterase and the corresponding PNB esterase produced in recombinant *E. coli* strains appear functionally identical and structually the same at macroscale.

EXAMPLE 6

Hydrolysis of Loracarbef Nucleus PNB Ester by Partially Purified PNB Esterase Partially purified PNB esterase (2.5 mg based on specific activity and known turn-over number of the enzyme) prepared from *Escherichia coli* K12 DH5α/pNB106R cells, and treated with N-ethyl maleimide to inactivate residual β-lactamase, was added to a suspension of loracarbef-nucleus PNB ester (2.2% w/v) in 50 mM Tris buffer, pH 8.0. The reaction mixture was maintained at 37° C. for 3 hours. Sodium hydroxide solution was added periodically to maintain the pH at 8.0. After 3 hours there was a 90% yield of loracarbef-nucleus free acid, based on high performance liquid chromatography (HPLC) analysis for that compound. Further incubation did not increase the yield.

EXAMPLE 7

Isolation and Purification of PNB Esterase from *Bacillus subtilis*

A. Preparation of Cell-Free Extract

A culture of *Bacillus subtilis* NRRL B-8079 was harvested and frozen by conventional methods. The frozen *B. subtilis* cells (760 g) were thawed and homogenized in 2 liters of Buffer A (10 mM potassium phosphate, pH 7.0; 1 mM 2 mercaptoethanol (2-ME); and 0.5 mM EDTA). The cell free extract was obtained by centrifugation at 24,000×g for 30 minutes. Protamine sulfate was added to the extract at a final concentration of 2.0 mg/ml and the mixture was stirred for 1 hour. The precipitates formed were removed by centrifugation. The supernatant was used as the cell-free extract in the following isolation procedure.

B. Isolation of Crude PNB Esterase

The extract was subjected to ammonium sulfate fractionation. The precipitates formed between 45–80% ammonium sulfate saturation were collected by centrifugation and dissolved in Buffer A, and then dialyzed overnight against the same buffer. The dialyzed sample was acidified to pH 5.0 with 1 N acetic acid, incubated for 10 minutes and subjected to centrifugation to remove the precipitates. The supernatant contained the crude PNB esterase.

C. Purification of PNB esterase

The supernatant was adjusted to pH 8.5 with 2N NH₄OH an applied onto a weak anionic resin (DE52 column, 3.7×35

TABLE 1

Purification of PNB esterase from *E. coli* K12 DH5α/pNB106R

| Step | Protein (mg) | Activity to loracarbef nucleus (mUnits) | Activity of β-lactamase (mUnits) | Activity ratio of esterase/β-lactamase | Sp. activity of esterase (mUnits/mg) | Fold | Yield (%) |
|---|---|---|---|---|---|---|---|
| cell free extract | 207.7 | 39658.7 | 669.3 | 59.3 | 190.9 | 1 | 100 |
| pH 5 treatment | 188.5 | 41703.2 | 672.3 | 62.0 | 212.2 | 1.16 | |
| Ammonium sulfate fractionation (45%–85%) | 123.5 | 28200.0 | 488.5 | 57.7 | 228.3 | 1.2 | 71 |
| DE-52 | 33.30 | 24503.0 | 3.89 | 6299 | 735.8 | 3.85 | 62 |
| p-Aminobenzamidine agarose | 20.57 | 23813.2 | 0 | | 1157.6 | 6.06 | 60 |
| Q-sepharose | 10.08 | 13552.0 | 0 | | 1344.4 | 7.04 | 34 |

Starting cell mass = 5.4 g wet weight
Substrate = loracarbef nucleus PNB ester cm; Pharmacia, Inc., Piscataway, N.J. 08854) equilibrated with Buffer B (10 mM Tris-HCl, pH 8.5; 50 mM NaCl; 1 mM 2-ME; and 0.5 mM EDTA). The column was washed with 350 ml of Buffer B and again with 1,750 ml of Buffer C (10 mM Tris-HCl, pH 7.0; 50 mM NaCl; 1 mM 2-ME; and 0.5 mM EDTA). The PNB esterase was eluted with a 3,500 ml gradient of 50–300 mM NaCl in Buffer C. Fractions of the PNB esterase were pooled and concentrated by ultrafiltration with an AMICON PM-10 membrane (Amicon, Danvers, Mass. 01923). The concentrated crude PNB esterase solution was subjected to gel filtration employing a polysaccharide-type gel (Sephacryl S-200 HR column, 5.0×95 cm; Pharmacia, Inc.) equilibrated with Buffer D (10 mM Tris-HCl, pH 8.0; 1 mM 2-ME; and 0.5 mM EDTA). The fractions containing enzyme activity were combined, concentrated by ultrafiltration and dialyzed overnight against Buffer B. The dialyzed solution was applied onto an anionic exchange resin, (Q-Sepharose column, 2.6×20 cm; Pharmacia Inc,) equilibrated with Buffer B. The column was washed with 100 ml of Buffer B and subsequently with 500 ml of Buffer E (10 mM MES-NaOH, pH 6.0; 10 mM NaCl; 1 mM 2-ME; and 0.5 mM EDTA). The PNB esterase was eluted with a 1,500 ml linear gradient of 100–300 mM NaCl in Buffer E. The fractions containing the PNB esterase were combined, concentrated by ultrafiltration, and dialyzed overnight against 10 mM sodium acetate, pH 5.0, containing 1 mM 2-ME and 0.5 mM EDTA.

After removing the precipitate by centrifugation, the enzyme solution was loaded onto a calcium phosphate-cellulose column (1.6×20) equilibrated with a buffer containing 10 mM sodium acetate, pH 5.0, containing 1 mM 2-ME and 0.5 mM EDTA. The finely-divided calcium phosphate used can be prepared according to Jenner, U.S. Pat. No. 3,737,516. After the column was washed with 250 ml of the same buffer, the PNB esterase was eluted with a 250 ml linear gradient of 10–50 mM potassium phosphate, pH 7.0, containing 1 mM 2-ME and 0.5 mM EDTA. The fractions containing the PNB esterase activity were pooled, concentrated by ultrafiltration, and then dialyzed overnight against Buffer D.

The dialyzed enzyme solution was applied onto a p-aminobenzamidine-agarose column (1.0×20 cm; Pharmacia Inc.) equilibrated with Buffer D. After washing the column with 50 ml of Buffer D, the PNB esterase was eluted with 100 ml linear gradient of 0–300 mM NaCl in Buffer D. The fractions with the PNB esterase activity eluted approximately between 160 and 220 mM NaCl in Buffer D were pooled, concentrated by ultrafiltration, and represented the purified enzyme.

All steps of the above-described purification were performed at temperatures between 0°–4° C. The progress of the purification was followed by assaying the material for PNB esterase activity obtained in each step of the isolation and purification.

TABLE 2

Purification of PNB Esterase from B. subtilis

| Step | Protein (mg) | Activity (U) | | | Specific Activity (mU/mg) | | | Ratio | |
|---|---|---|---|---|---|---|---|---|---|
| | | Lora | Ceph | p-NPA | Lora | Ceph | p-NPA | Ceph/Lora | p-NPA/Lora |
| Cell-free extract | 130000 | 271 | 14.8 | 18900 | 2.10 | 0.114 | 145 | 0.054 | 69 |
| Ammonium sulfate (45–80%) | 72600 | 54.0 | 4.08 | 5320 | 0.74 | 0.056 | 73.5 | 0.076 | 99 |
| pH treatment (pH 5) | 29100 | 54.4 | 4.53 | 5234 | 1.87 | 0.155 | 180 | 0.083 | 96 |
| DE 52 | 3450 | 181 | 10.8 | 3710 | 52.5 | 3.13 | 1080 | 0.060 | 20 |
| Sephacryl S-200 | 1440 | 115 | 11.3 | 4460 | 79.5 | 7.87 | 3170 | 0.098 | 40 |
| Q-Sepharose (pH 8) | 164 | 122 | 7.0 | 3690 | 742 | 42.7 | 22500 | 0.058 | 30 |
| Calcium phosphate cellulose | 32.4 | 54.8 | 2.3 | 3320 | 1690 | 71.0 | 102000 | 0.042 | 60 |
| p-Amino benzamidine agarose | 24.8 | 33.0 | 1.46 | 2580 | 1330 | 58.8 | 104000 | 0.044 | 78 |
| Q-Sepharose pH 6 | 2.67 | 5.9 | 0.26 | 221 | 2210 | 97.5 | 82800 | 0.044 | 37 |

Substrates used:
Lora = loracarbef-PNB
Ceph = Cephalexin-PNB
p-NPA = p-Nitrophenyl acetate D. Assay Method for PNB Esterase Activity A 1 ml reaction mixture containing 5 μmoles Bis-Tri-Propane-HCl, pH 6.5, 0.5 μmole substrate, and appropriate amounts of enzyme solution was incubated at 30° C. in a constant-temperature shaker for 30 min. The reaction was stopped by the addition of an equal volume of acetonitrile. The mixture was then centrifuged to remove the protein and the supernatant solution was analyzed by high performance liquid chromatography (HPLC) for product formation and substrate disappearance. The HPLC was performed in a C-18 reverse-phase column (Beckman Ultrosphere ODS, Beckman Instruments Inc., Fullerton, Calif. 92634) with a linear gradient formed by Buffer A containing 80% of 1 mM Triethylamine-HCl, pH 2.5 and 20% methanol and Buffer B containing methanol, at a flow rate of 1 ml/min.

The HPLC system used was a Varian HPLC System including a Vista 5560 unit (Varian Associates, Sugar Land TX) and a model 230-401 auto-sampling injector (Gilson Medical Electronics, Middleton, Wis.). The PNB esterase activity was determined by monitoring product formation at 254 nm.

Taking advantage of the absorption change in the hydrolysis of p-nitrophenylacetate to p-nitrophenyl alcohol and acetate, a spectrophotometric assay for PNB esterase was developed. An enzyme fraction showing activity in this assay may not necessarily have the PNB esterase activity, but the PNB esterase will show activity in this assay. For the purified PNB esterase, the results of this assay correlated well with that of the HPLC assay. Thus, this assay is valuable in the purification of the enzyme, where large numbers of assays are generally involved. This assay was carried out at room temperature in a 1 ml assay mixture, containing 100 μM Tris-HCl (pH 7.0), 1.6 μM p-nitrophenylacetate and 1–20 μl enzyme solution. The activity was followed by measuring the absorption change at 405 nm in either a Cary spectrophotometer, model 219 or Beckman DU-50.

SEQUENCE LISTING ( 1 ) GENERAL INFORMATION:

( i i i ) NUMBER OF SEQUENCES:7

( 2 ) INFORMATION FOR SEQ ID NO:1:

( i ) SEQUENCE CHARACTERISTICS:
( A ) LENGTH:1470 nucleotides
( B ) TYPE:nucleic acid
( C ) STRANDEDNESS:double
( D ) TOPOLOGY:linear ( i i ) MOLECULE TYPE:DNA ( x i ) SEQUENCE DESCRIPTION:SEQ ID NO:1:

| | | | | | | | | | | | | | |
|---|---|---|---|---|---|---|---|---|---|---|---|---|---|
| ATG | ACT | CAT | CAA | ATA | GTA | ACG | ACT | CAA | TAC | GGC | AAA | GTA | AAA | 42 |
| GGC | ACA | ACG | GAA | AAC | GGC | GTA | CAT | AAG | TGG | AAA | GGC | ATC | CCC | 84 |
| TAT | GCC | AAG | CCG | CCT | GTC | GGA | CAA | TGG | CGT | TTT | AAA | GCA | CCT | 126 |
| GAG | CCG | CCT | GAA | GTG | TGG | GAA | GAT | GTC | CTT | GAT | GCC | ACA | GCG | 168 |
| TAC | GGT | CCT | ATT | TGC | CCG | CAG | CCG | TCT | GAT | TTG | CTC | TCA | CTG | 210 |
| TCG | TAT | ACA | GAG | CTG | CCC | CGC | CAG | TCC | GAG | GAT | TGC | TTG | TAT | 252 |
| GTC | AAT | GTA | TTT | GCG | CCT | GAC | ACT | CCA | AGT | CAA | AAT | CTT | CCT | 294 |
| GTC | ATG | GTG | TGG | ATT | CAC | GGA | GGC | GCT | TTT | TAT | CTT | GGA | GCG | 336 |
| GGC | AGT | GAG | CCA | TTG | TAT | GAC | GGA | TCA | AAA | CTT | GCG | GCA | CAG | 378 |
| GGA | GAA | GTC | ATT | GTC | GTT | ACA | TTG | AAC | TAT | CGG | CTG | GGG | CCG | 420 |
| TTT | GGC | TTT | TTG | CAC | TTG | TCT | TCG | TTT | GAT | GAG | GCG | TAT | TCC | 462 |
| GAT | AAC | CTT | GGG | CTT | TTA | GAC | CAA | GCC | GCC | GCG | CTG | AAA | TGG | 504 |
| GTG | CGG | GAG | AAT | ATC | TCA | GCG | TTT | GGC | GGT | GAT | CCC | GAT | AAC | 546 |
| GTA | ACA | GTA | TTT | GGA | GAA | TCC | GCC | GGC | GGC | ATG | AGC | ATT | GCC | 588 |
| GCG | CTG | CTC | GCT | ATG | CCT | GCG | GCA | AAA | GGC | CTG | TTC | CAG | AAA | 630 |
| GCG | ATC | ATG | GAA | AGC | GGC | GCT | TCC | CGA | ACA | ATG | ACA | AAA | GAA | 672 |
| CAA | GCG | GCA | AGC | ACT | GCG | GCT | GCC | TTT | TTA | CAG | GTC | CTT | GGG | 714 |
| ATT | AAT | GAG | AGC | CAG | CTG | GAC | AGA | TTG | CAT | ACT | GTA | GCA | GCG | 756 |
| GAA | GAT | TTG | CTT | AAA | GCG | GCC | GAT | CAG | CTT | CGG | ATT | GCA | GAA | 798 |
| AAA | GAA | AAT | ATC | TTT | CAG | CTG | TTC | TTC | CAG | CCC | GCC | CTT | GAT | 840 |
| CCG | AAA | ACG | CTG | CCT | GAA | GAA | CCA | GAA | AAA | TCG | ATC | GCA | GAA | 882 |
| GGG | GCT | GCT | TCC | GGC | ATT | CCG | CTA | TTG | ATT | GGA | ACA | ACC | CGT | 924 |
| GAT | GAA | GGA | TAT | TTA | TTT | TTC | ACC | CCG | GAT | TCA | GAC | GTT | CAT | 966 |
| TCT | CAG | GAA | ACG | CTT | GAT | GCA | GCA | CTC | GAG | TAT | TTA | CTA | GGG | 1008 |
| AAG | CCG | CTG | GCA | GAG | AAA | GCT | GCC | GAT | TTG | TAT | CCG | CGT | TCT | 1050 |
| CTG | GAA | AGC | CAA | ATT | CAT | ATG | ATG | ACT | GAT | TTA | TTA | TTT | TGG | 1092 |

```
CGC  CCT  GCC  GTC  GCC  TAT  GCA  TCC  GCA  CAG  TCT  CAT  TAC  GCC                1134

CCT  GTC  TGG  ATG  TAC  CGG  TTC  GAT  TGG  CAC  CCG  GAG  AAG  CCG                1176

CCG  TAC  AAT  AAA  GCG  TTT  CAC  GCA  TTA  GAG  CTT  CCT  TTT  GTC                1218

TTT  GGA  AAT  CTG  GAC  GGA  TTG  GAA  CGA  ATG  GCA  AAA  GCG  GAG                1260

ATT  ACG  GAT  GAG  GTG  AAA  CAG  CTT  TCT  CAC  ACG  ATA  CAA  TCC                1302

GCG  TGG  ATC  ACG  TTC  GCT  AAA  ACA  GGA  AAC  CCA  AGC  ACC  GAA                1344

GCT  GTG  AAT  TGG  CCG  GCG  TAT  CAT  GAA  GAA  ACG  AGA  GAG  ACG                1386

GTG  ATT  TTA  GAC  TCA  GAG  ATT  ACG  ATC  GAA  AAC  GAT  CCC  GAA                1428

TCT  GAA  AAA  AGG  CAG  AAG  CTA  TTC  CCT  TCA  AAA  GGA  GAA  TAA                1470
```

( 2 ) INFORMATION FOR SEQ ID NO:2:

( i ) SEQUENCE CHARACTERISTICS:
      ( A ) LENGTH:489 amino acids
      ( B ) TYPE:amino acid
      ( C ) STRANDEDNESS:single
      ( D ) TOPOLOGY:linear ( i i ) MOLECULE TYPE:protein ( x i ) SEQUENCE DESCRIPTION:SEQ ID NO:2:

```
Met  Thr  His  Gln  Ile  Val  Thr  Thr  Gln  Tyr  Gly  Lys  Val  Lys  Gly
 1                  5                   10                          15

Thr  Thr  Glu  Asn  Gly  Val  His  Lys  Trp  Lys  Gly  Ile  Pro  Tyr  Ala
                    20                  25                          30

Lys  Pro  Pro  Val  Gly  Gln  Trp  Arg  Phe  Lys  Ala  Pro  Glu  Pro  Pro
                    35                  40                          45

Glu  Val  Trp  Glu  Asp  Val  Leu  Asp  Ala  Thr  Ala  Tyr  Gly  Pro  Ile
                    50                  55                          60

Cys  Pro  Gln  Pro  Ser  Asp  Leu  Leu  Ser  Leu  Ser  Tyr  Thr  Glu  Leu
                    65                  70                          75

Pro  Arg  Gln  Ser  Glu  Asp  Cys  Leu  Tyr  Val  Asn  Val  Phe  Ala  Pro
                    80                  85                          90

Asp  Thr  Pro  Ser  Gln  Asn  Leu  Pro  Val  Met  Val  Trp  Ile  His  Gly
                    95                  100                         105

Gly  Ala  Phe  Tyr  Leu  Gly  Ala  Gly  Ser  Glu  Pro  Leu  Tyr  Asp  Gly
                    110                 115                         120

Ser  Lys  Leu  Ala  Ala  Gln  Gly  Glu  Val  Ile  Val  Thr  Leu  Asn
                    125                 130                         135

Tyr  Arg  Leu  Gly  Pro  Phe  Gly  Phe  Leu  His  Leu  Ser  Ser  Phe  Asp
                    140                 145                         150

Glu  Ala  Tyr  Ser  Asp  Asn  Leu  Gly  Leu  Leu  Asp  Gln  Ala  Ala  Ala
                    155                 160                         165

Leu  Lys  Trp  Val  Arg  Glu  Asn  Ile  Ser  Ala  Phe  Gly  Gly  Asp  Pro
                    170                 175                         180

Asp  Asn  Val  Thr  Val  Phe  Gly  Glu  Ser  Ala  Gly  Gly  Met  Ser  Ile
                    185                 190                         195

Ala  Ala  Leu  Leu  Ala  Met  Pro  Ala  Ala  Lys  Gly  Leu  Phe  Gln  Lys
                    200                 205                         210

Ala  Ile  Met  Glu  Ser  Gly  Ala  Ser  Arg  Thr  Met  Thr  Lys  Glu  Gln
                    215                 220                         225

Ala  Ala  Ser  Thr  Ala  Ala  Ala  Phe  Leu  Gln  Val  Leu  Gly  Ile  Asn
                    230                 235                         240
```

| | | | | | | | | | | | | | | |
|---|---|---|---|---|---|---|---|---|---|---|---|---|---|---|
| Glu | Ser | Gln | Leu | Asp<br>245 | Arg | Leu | His | Thr | Val<br>250 | Ala | Ala | Glu | Asp | Leu<br>255 |
| Leu | Lys | Ala | Ala | Asp<br>260 | Gln | Leu | Arg | Ile | Ala<br>265 | Glu | Lys | Glu | Asn | Ile<br>270 |
| Phe | Gln | Leu | Phe | Phe<br>275 | Gln | Pro | Ala | Leu | Asp<br>280 | Pro | Lys | Thr | Leu | Pro<br>285 |
| Glu | Glu | Pro | Glu | Lys<br>290 | Ser | Ile | Ala | Glu | Gly<br>295 | Ala | Ala | Ser | Gly | Ile<br>300 |
| Pro | Leu | Leu | Ile | Gly<br>305 | Thr | Thr | Arg | Asp | Glu<br>310 | Gly | Tyr | Leu | Phe | Phe<br>315 |
| Thr | Pro | Asp | Ser | Asp<br>320 | Val | His | Ser | Gln | Glu<br>325 | Thr | Leu | Asp | Ala | Ala<br>330 |
| Leu | Glu | Tyr | Leu | Leu<br>335 | Gly | Lys | Pro | Leu | Ala<br>340 | Glu | Lys | Ala | Ala | Asp<br>345 |
| Leu | Tyr | Pro | Arg | Ser<br>350 | Leu | Glu | Ser | Gln | Ile<br>355 | His | Met | Met | Thr | Asp<br>360 |
| Leu | Leu | Phe | Trp | Arg<br>365 | Pro | Ala | Val | Ala | Tyr<br>370 | Ala | Ser | Ala | Gln | Ser<br>375 |
| His | Tyr | Ala | Pro | Val<br>380 | Trp | Met | Tyr | Arg | Phe<br>385 | Asp | Trp | His | Pro | Glu<br>390 |
| Lys | Pro | Pro | Tyr | Asn<br>395 | Lys | Ala | Phe | His | Ala<br>400 | Leu | Glu | Leu | Pro | Phe<br>405 |
| Val | Phe | Gly | Asn | Leu<br>410 | Asp | Gly | Leu | Glu | Arg<br>415 | Met | Ala | Lys | Ala | Glu<br>420 |
| Ile | Thr | Asp | Glu | Val<br>425 | Lys | Gln | Leu | Ser | His<br>430 | Thr | Ile | Gln | Ser | Ala<br>435 |
| Trp | Ile | Thr | Phe | Ala<br>440 | Lys | Thr | Gly | Asn | Pro<br>445 | Ser | Thr | Glu | Ala | Val<br>450 |
| Asn | Trp | Pro | Ala | Tyr<br>455 | His | Glu | Glu | Thr | Arg<br>460 | Glu | Thr | Val | Ile | Leu<br>465 |
| Asp | Ser | Glu | Ile | Thr<br>470 | Ile | Glu | Asn | Asp | Pro<br>475 | Glu | Ser | Glu | Lys | Arg<br>480 |
| Gln | Lys | Leu | Phe | Pro<br>485 | Ser | Lys | Gly | Glu<br>489 | | | | | | |

( 2 ) INFORMATION FOR SEQ ID NO:3:

( i ) SEQUENCE CHARACTERISTICS:
    ( A ) LENGTH:22 amino acids
    ( B ) TYPE:amino acid
    ( C ) STRANDEDNESS:single
    ( D ) TOPOLOGY:linear ( i i ) MOLECULE TYPE:peptide ( x i ) SEQUENCE DESCRIPTION:SEQ ID NO:3:

| | | | | | | | | | | | | | |
|---|---|---|---|---|---|---|---|---|---|---|---|---|---|
| Met<br>5 | Thr | His | Gln | Ile | Val<br>10 | Thr | Thr | Tyr | Gly | Lys<br>15 | Lys | Val | Lys | Gly |
| Thr<br>20 | Gln | Glu | Asn | Gly | Val | His | | | | | | | | |

( 2 ) INFORMATION FOR SEQ ID NO:4:

( i ) SEQUENCE CHARACTERISTICS:
    ( A ) LENGTH:41 nucleotides
    ( B ) TYPE:nucleic acid
    ( C ) STRANDEDNESS:single
    ( D ) TOPOLOGY:linear (ii) MOLECULE TYPE:DNA (xi) SEQUENCE DESCRIPTION:SEQ ID NO:4:

ATGACACATC AAATTGTCAC AACATATGGC AAAAAAGTCA A   41

(2) INFORMATION FOR SEQ ID NO:5:

(i) SEQUENCE CHARACTERISTICS:
        (A) LENGTH:41 nucleotides
        (B) TYPE:nucleic acid
        (C) STRANDEDNESS:single
        (D) TOPOLOGY:linear (ii) MOLECULE TYPE:DNA (xi) SEQUENCE DESCRIPTION:SEQ ID NO:5:

TATGGCAAAA AAGTCAAAGG CACACAAGAA AATGGCGTCC A   41

(2) INFORMATION FOR SEQ ID NO:6:

(i) SEQUENCE CHARACTERISTICS:
        (A) LENGTH:34 nucleotides
        (B) TYPE:nucleic acid
        (C) STRANDEDNESS:single
        (D) TOPOLOGY:linear (ii) MOLECULE TYPE:DNA (xi) SEQUENCE DESCRIPTION:SEQ ID NO:6:

AAAAAGGGAG AGAACCATAT GACTCATCAA ATAG   34

(2) INFORMATION FOR SEQ ID NO:7:

(i) SEQUENCE CHARACTERISTICS:
        (A) LENGTH:20 nucleotides
        (B) TYPE:nucleic acid
        (C) STRANDEDNESS:single
        (D) TOPOLOGY:linear (ii) MOLECULE TYPE:DNA (xi) SEQUENCE DESCRIPTION:SEQ ID NO:7:

TTGACATACA AGCAATCCTC   20

We claim:

1. An isolated DNA compound that encodes *Bacillus subtilis* para-nitrobenzyl (PNB) esterase of the amino acid sequence:

Met Thr His Gln Ile Val Thr Thr Gln Tyr Gly Lys Val Lys Gly
1          5          10          15

Thr Thr Glu Asn Gly Val His Lys Trp Lys Gly Ile Pro Tyr Ala
          20          25          30

Lys Pro Pro Val Gly Gln Trp Arg Phe Lys Ala Pro Glu Pro Pro
          35          40          45

Glu Val Trp Glu Asp Val Leu Asp Ala Thr Ala Tyr Gly Pro Ile
          50          55          60

Cys Pro Gln Pro Ser Asp Leu Leu Ser Leu Ser Tyr Thr Glu Leu
          65          70          75

Pro Arg Gln Ser Glu Asp Cys Leu Tyr Val Asn Val Phe Ala Pro
          80          85          90

-continued

Asp Thr Pro Ser Gln Asn Leu Pro Val Met Val Trp Ile His Gly
          95          100         105

Gly Ala Phe Tyr Leu Gly AlaGly Ser Glu Pro Leu Tyr Asp Gly
          110         115         120

Ser Lys Leu Ala Ala Gln Gly Glu Val Ile Val Val Thr Leu Asn
          125         130         135

Tyr Arg Leu Gly Pro Phe Gly Phe Leu His Leu Ser Ser Phe Asp
          140         145         150

Glu Ala Tyr Ser Asp Asn Leu Gly Leu Leu Asp Gln Ala Ala Ala
          155         160         165

Leu Lys Trp Val Arg Glu Asn Ile Ser Ala Phe Gly Gly Asp Pro
          170         175         180

Asp Asn Val Thr Val Phe Gly Glu Ser Ala Gly Gly Met Ser Ile
          185         190         195

Ala Ala Leu Leu Ala Met Pro Ala Ala Lys Gly Leu Phe Gln Lys
          200         205         210

-continued

Ala Ile Met Glu Ser Gly Ala Ser Arg Thr Met Thr Lys Glu Gln
215                 220                 225

Ala Ala Ser Thr Ala Ala AlaPhe Leu Gln Val Leu Gly Ile Asn
230                 235                 240

Glu Ser Gln Leu Asp Arg Leu His Thr Val Ala Ala Glu Asp Leu
245                 250                 255

Leu Lys Ala Ala Asp Gln Leu Arg Ile Ala Glu Lys Glu Asn Ile
260                 265                 270

Phe Gln Leu Phe Gln ProAla Leu Asp Pro Lys Thr Leu Pro
275                 280                 285

Glu Glu Pro Glu Lys Ser Ile Ala Glu Gly Ala Ala Ser Gly Ile
290                 295                 300

Pro Leu Leu Ile Gly Thr Thr Arg Asp Glu Gly Tyr Leu Phe Phe
305                 310                 315

Thr Pro Asp Ser Asp Val His Ser Gln Glu Thr Leu Asp Ala Ala
320                 325                 330

Leu Glu Tyr Leu Leu Gly Lys Pro Leu Ala Glu Lys Ala Ala Asp
335                 340                 345

Leu Tyr Pro Arg Ser Leu Glu Ser Gln Ile His Met Met Thr Asp
350                 355                 360

Leu Leu Phe Trp Arg Pro AlaVal Ala Tyr Ala Ser Ala Gln Ser
365                 370                 375

His Tyr Ala Pro Val Trp Met Tyr Arg Phe Asp Trp His Pro Glu
380                 385                 390

Lys Pro Pro Tyr Asn Lys Ala Phe His Ala Leu Glu Leu Pro Phe
395                 400                 405

-continued

Val Phe Gly Asn Leu Asp Gly Leu Glu Arg Met Ala Lys Ala Glu
410                 415                 420

Ile Thr Asp Glu Val Lys Gln Leu Ser His Thr Ile Gln Ser Ala
425                 430                 435

Trp Ile Thr Phe Ala Lys Thr Gly Asn Pro Ser Thr Glu Ala Val
440                 445                 450

Asn Trp Pro Ala Tyr His GluGlu Thr Arg Glu Thr Val Ile Leu
455                 460                 465

Asp Ser Glu Ile Thr Ile GluAsn Asp Pro Glu Ser Glu Lys Arg
470                 475                 480

Gln Lys Leu Phe Pro Ser Lys Gly Glu
485                 489 wherein Ala is an alanine residue, Arg is an arginine residue, Asn is an asparagine residue, Asp is an aspartic acid residue, Cys is a cysteine residue, Gln is a glutamine residue, Glu is a glutamic acid residue, Gly is a glycine residue, His is a histidine residue, Ile is an isoleucine residue, Leu is a leucine residue, Lys is a lysine residue, Met is a methionine residue, Phe is a phenylalanine residue, Pro is a proline residue, Ser is a serine residue, Thr is a threonine residue, Trp is a tryptophan residue, Tyr is a tyrosine residue, and Val is a valine residue.

2. The isolated DNA compound of claim 1 wherein the coding strand comprises the DNA sequence (SEQ ID NO: 2):

| ATG | ACT | CAT | CAA | ATA | GTA | ACG | ACT | CAA | TAC | GGC | AAA | GTA | AAA | 42 |
|---|---|---|---|---|---|---|---|---|---|---|---|---|---|---|
| GGC | ACA | ACG | GAA | AAC | GGC | GTA | CAT | AAG | TGG | AAA | GGC | ATC | CCC | 84 |
| TAT | GCC | AAG | CCG | CCT | GTC | GGA | CAA | TGG | CGT | TTT | AAA | GCA | CCT | 126 |
| GAG | CCG | CCT | GAA | GTG | TGG | GAA | GAT | GTC | CTT | GAT | GCC | ACA | GCG | 168 |
| TAC | GGT | CCT | ATT | TGC | CCG | CAG | CCG | TCT | GAT | TTG | CTC | TCA | CTG | 210 |
| TCG | TAT | ACA | GAG | CTG | CCC | CGC | CAG | TCC | GAG | GAT | TGC | TTG | TAT | 252 |
| GTC | AAT | GTA | TTT | GCG | CCT | GAC | ACT | CCA | AGT | CAA | AAT | CTT | CCT | 294 |
| GTC | ATG | GTG | TGG | ATT | CAC | GGA | GGC | GCT | TTT | TAT | CTT | GGA | GCG | 336 |
| GGC | AGT | GAG | CCA | TTG | TAT | GAC | GGA | TCA | AAA | CTT | GCG | GCA | CAG | 378 |
| GGA | GAA | GTC | ATT | GTC | GTT | ACA | TTG | AAC | TAT | CGG | CTG | GGG | CCG | 420 |
| TTT | GGC | TTT | TTG | CAC | TTG | TCT | TCG | TTT | GAT | GAG | GCG | TAT | TCC | 462 |
| GAT | AAC | CTT | GGG | CTT | TTA | GAC | CAA | GCC | GCC | GCG | CTG | AAA | TGG | 504 |
| GTG | CGG | GAG | AAT | ATC | TCA | GCG | TTT | GGC | GGT | GAT | CCC | GAT | AAC | 546 |
| GTA | ACA | GTA | TTT | GGA | GAA | TCC | GCC | GGC | GGC | ATG | AGC | ATT | GCC | 588 |
| GCG | CTG | CTC | GCT | ATG | CCT | GCG | GCA | AAA | GGC | CTG | TTC | CAG | AAA | 630 |
| GCG | ATC | ATG | GAA | AGC | GGC | GCT | TCC | CGA | ACA | ATG | ACA | AAA | GAA | 672 |
| CAA | GCG | GCA | AGC | ACT | GCG | GCT | GCC | TTT | TTA | CAG | GTC | CTT | GGG | 714 |
| ATT | AAT | GAG | AGC | CAG | CTG | GAC | AGA | TTG | CAT | ACT | GTA | GCA | GCG | 756 |
| GAA | GAT | TTG | CTT | AAA | GCG | GCC | GAT | CAG | CTT | CGG | ATT | GCA | GAA | 798 |
| AAA | GAA | AAT | ATC | TTT | CAG | CTG | TTC | TTC | CAG | CCC | GCC | CTT | GAT | 840 |
| CCG | AAA | ACG | CTG | CCT | GAA | GAA | CCA | GAA | AAA | TCG | ATC | GCA | GAA | 882 |
| GGG | GCT | GCT | TCC | GGC | ATT | CCG | CTA | TTG | ATT | GGA | ACA | ACC | CGT | 924 |
| GAT | GAA | GGA | TAT | TTA | TTT | TTC | ACC | CCG | GAT | TCA | GAC | GTT | CAT | 966 |
| TCT | CAG | GAA | ACG | CTT | GAT | GCA | GCA | CTC | GAG | TAT | TTA | CTA | GGG | 1008 |
| AAG | CCG | CTG | GCA | GAG | AAA | GCT | GCC | GAT | TTG | TAT | CCG | CGT | TCT | 1050 |
| CTG | GAA | AGC | CAA | ATT | CAT | ATG | ATG | ACT | GAT | TTA | TTA | TTT | TGG | 1092 |
| CGC | CCT | GCC | GTC | GCC | TAT | GCA | TCC | GCA | CAG | TCT | CAT | TAC | GCC | 1134 |
| CCT | GTC | TGG | ATG | TAC | CGG | TTC | GAT | TGG | CAC | CCG | GAG | AAG | CCG | 1176 |
| CCG | TAC | AAT | AAA | GCG | TTT | CAC | GCA | TTA | GAG | CTT | CCT | TTT | GTC | 1218 |
| TTT | GGA | AAT | CTG | GAC | GGA | TTG | GAA | CGA | ATG | GCA | AAA | GCG | GAG | 1260 |
| ATT | ACG | GAT | GAG | GTG | AAA | CAG | CTT | TCT | CAC | ACG | ATA | CAA | TCC | 1302 |
| GCG | TGG | ATC | ACG | TTC | GCT | AAA | ACA | GGA | AAC | CCA | AGC | ACC | GAA | 1344 |
| GCT | GTG | AAT | TGG | CCG | GCG | TAT | CAT | GAA | GAA | ACG | AGA | GAG | ACG | 1386 |
| GTG | ATT | TTA | GAC | TCA | GAG | ATT | ACG | ATC | GAA | AAC | GAT | CCC | GAA | 1428 |
| TCT | GAA | AAA | AGG | CAG | AAG | CTA | TTC | CCT | TCA | AAA | GGA | GAA | TAA | 1470 | wherein A is a deoxyadenyl residue, G is a deoxyguanyl residue, C is a deoxycytidyl residue, and T is a thymidyl residue.

3. A recombinant DNA vector that comprises the DNA sequence (SEQ ID NO: 1) of claim 1.

4. A recombinant DNA vector of claim 3 that further comprises a promoter positioned to drive expression of said PNB esterase activity encoding DNA.

5. A recombinant DNA vector of claim 4 wherein said promoter functions in *Escherichia coli*.

6. A recombinant DNA expression vector of claim 5 that is plasmid pNB106R or pNB106RM.

7. The recombinant DNA expression vector of claim 6 that is plasmid pNB106R.

8. The recombinant DNA expression vector of claim 6 that is plasmid pNB106RM.

9. A host cell transformed with the recombinant DNA vector of claim 3.

10. A transformed host cell of claim 9 that is *Escherichia coli*.

11. A transformed host cell of claim 10 that is selected from the group consisting of *Escherichia coli* K12 RV308/pNB106R, *Escherichia coli* K12 RV308/pNB106RM, *Escherichia coli* K12 DH5α/pNB106R, *Escherichia coli* K12 DH5α/pNB106RM, *Escherichia coli* W ATCC 11105/pNB106R, and *Escherichia coli* W ATCC 11105/pNB106RM.

12. The transformed host cell of claim 11 that is *Escherichia coli* K12 RV308/pNB106R.

13. The transformed host cell of claim 11 that is *Escherichia coli* K12 RV308/pNB106RM.

14. The transformed host cell of claim 11 that is *Escherichia coli* K12 DH5α/pNB106R.

15. The transformed host cell of claim 11 that is *Escherichia coli* K12 DH5α/pNB106RM.

16. The transformed host cell of claim 11 that is *Escherichia coli* W ATCC 11105/pNB106R.

17. The transformed host cell of claim 11 that is *Escherichia coli* W ATCC 11105/pNB106RM.

18. A method for constructing a recombinant host cell capable of expressing PNB esterase activity, said method comprising:

transforming said host cell with a recombinant DNA expression vector that comprises:
(a) a promoter and translational activating sequence that functions in said host cell
(b) a DNA sequence of claim 1 encoding PNB esterase activity of *Bacillus subtilis* positioned for the expression from said promoter and translational activating sequence.

19. A method of using a host cell constructed by the method of claim 18, for expressing PNB esterase activity, said method comprising: culturing said host cell under conditions suitable for gene expression.

20. The method of claim 19 wherein said recombinant host cell is selected from the group consisting of *Escherichia coli* K12 RV308/pNB106R, *Escherichia coli* K12 RV308/pNB106RM, *Escherichia coli* K12 DH5α/pNB106R, *Escherichia coli* K12 DH5α/pNB106RM, *Escherichia coli* W ATCC 11105/pNB106R, and *Escherichia coli* W ATCC 11105/pNB106RM.

21. The method of claim 20 wherein said recombinant host cell is *Escherichia coli* K12 RV308/pNB106R.

22. The method of claim 20 wherein said recombinant host cell is *Escherichia coli* K12 RV308/pNB106RM.

23. The method of claim 20 wherein said recombinant host cell is *Escherichia coli* K12 DH5α/pNB106R.

24. The method of claim 20 wherein said recombinant host cell is *Escherichia coli* K12 DH5α/pNB106RM.

25. The method of claim 20 wherein said recombinant host cell is *Escherichia coli* K12 W ATCC 11105/pNB106R.

26. The method of claim 20 wherein said recombinant host cell is *Escherichia coli* K12 W ATCC 11105/pNB106RM.

* * * * *